(12) United States Patent
Barberio

(10) Patent No.: US 10,524,936 B2
(45) Date of Patent: Jan. 7, 2020

(54) POROUS ORTHOPEDIC OR PROSTHETIC SUPPORT HAVING REMOVABLE CUSHIONING AND SCAFFOLDING LAYERS

(71) Applicant: Alessandro Barberio, Aurora (CA)

(72) Inventor: Alessandro Barberio, Aurora (CA)

( * ) Notice: Subject to any disclaimer, the term of this patent is extended or adjusted under 35 U.S.C. 154(b) by 782 days.

(21) Appl. No.: 15/110,299

(22) PCT Filed: Jan. 9, 2015

(86) PCT No.: PCT/CA2015/050014
§ 371 (c)(1),
(2) Date: Jul. 7, 2016

(87) PCT Pub. No.: WO2015/103708
PCT Pub. Date: Jul. 16, 2015

(65) Prior Publication Data
US 2016/0324666 A1    Nov. 10, 2016

Related U.S. Application Data

(60) Provisional application No. 62/124,956, filed on Jan. 9, 2015, provisional application No. 62/123,994, filed
(Continued)

(51) Int. Cl.
*A61F 2/78*     (2006.01)
*A61F 5/01*     (2006.01)
(Continued)

(52) U.S. Cl.
CPC ......... *A61F 2/7812* (2013.01); *A61F 2/7843* (2013.01); *A61F 2/80* (2013.01);
(Continued)

(58) Field of Classification Search
CPC ........ A61F 2/7812; A61F 2/80; A61F 2/7843; A61F 5/05858; A61F 5/05833;
(Continued)

(56) References Cited

U.S. PATENT DOCUMENTS 6,139,513 A * 10/2000 Grim .................... A61F 5/0111
                                                    602/41
6,482,491 B1   11/2002 Samuelsen et al.
(Continued)

FOREIGN PATENT DOCUMENTS

CA      2254492 A1    5/2000
CA      2355041 A1   10/2002
(Continued)

*Primary Examiner* — Tarla R Patel
(74) *Attorney, Agent, or Firm* — Heer Law; Christopher D. Heer

(57) ABSTRACT

An orthopedic or prosthetic support including at least three layers that allows for aeration and cushioning of the enclosed area is described herein. The orthopedic or prosthetic support includes an inner cushioning layer which is compressed against the skin in use. An intermediate scaffolding layer is situated substantially parallel to the inner cushioning layer and is maintained in spaced apart relationship with the inner cushioning layer by spacer members. An exterior layer overlays the intermediate scaffolding layer and may be either a flexible breathable fabric such as velvet or a thermoplastic with a plurality of perforations. The inner cushioning layer and the intermediate scaffolding layer include a plurality of perforations providing air pathways through the two layers. The grid-like arrangement of spacer members also define air passages between the inner and intermediate layers which further enhance circulation of exterior air to the skin covered by the orthopedic or prosthetic support.

13 Claims, 35 Drawing Sheets

Related U.S. Application Data on Dec. 5, 2014, provisional application No. 62/071,898, filed on Oct. 6, 2014, provisional application No. 61/998,832, filed on Jul. 10, 2014, provisional application No. 61/964,617, filed on Jan. 10, 2014.

(51) Int. Cl.
*A61F 5/058* (2006.01)
*A61F 2/80* (2006.01)

(52) U.S. Cl.
CPC .......... *A61F 5/0111* (2013.01); *A61F 5/0118* (2013.01); *A61F 5/0585* (2013.01); *A61F 5/05833* (2013.01); *A61F 5/05858* (2013.01); *A61F 2002/785* (2013.01)

(58) Field of Classification Search
CPC .... A61F 5/0118; A61F 5/0111; A61F 5/0585; A61F 2002/785
USPC .......................................................... 602/14
See application file for complete search history.

(56) References Cited

U.S. PATENT DOCUMENTS

| | | | |
|---|---|---|---|
| 6,553,994 | B2 | 4/2003 | Bard |
| 8,012,112 | B2 | 9/2011 | Barberio |
| 2002/0115972 | A1 | 8/2002 | Dabi et al. |
| 2004/0127838 | A1 | 7/2004 | Jeziak |
| 2004/0162511 | A1 | 8/2004 | Barberio |
| 2005/0010155 | A1 | 1/2005 | Chiang et al. |
| 2007/0191749 | A1* | 8/2007 | Barberio .................. A43B 7/08 602/23 |
| 2009/0018481 | A1 | 1/2009 | Bader |
| 2009/0093779 | A1 | 4/2009 | Riesinger |
| 2010/0268144 | A1 | 10/2010 | Lu et al. |
| 2011/0152735 | A1 | 6/2011 | Barberio |
| 2011/0183019 | A1 | 7/2011 | Seyler et al. |
| 2013/0012897 | A1 | 1/2013 | Collyer |

FOREIGN PATENT DOCUMENTS

| | | | | |
|---|---|---|---|---|
| CA | 2478159 | A1 * | 2/2006 | .......... A61F 5/0104 |
| CA | 2478159 | A1 | 2/2006 | |
| CA | 2478162 | A1 | 2/2006 | |
| CN | 202844054 | U | 4/2013 | |
| CN | 202960940 | U | 6/2013 | |
| CN | 203122770 | U | 8/2013 | |
| DE | 101 28 230 | A1 | 6/2002 | |
| DE | 20 2010 012704 | U1 | 12/2010 | |
| EP | 1496826 | A1 | 1/2005 | |
| EP | 1 640 032 | A1 | 3/2006 | |
| EP | 2253294 | A1 | 11/2010 | |
| FR | 2583636 | A1 | 12/1986 | |
| JP | 2000-213656 | A | 8/2000 | |
| JP | 2004-208972 | A | 7/2004 | |
| JP | 2010-131163 | A | 6/2010 | |
| WO | 2006/136024 | A1 | 12/2006 | |
| WO | 2009/047564 | A2 | 4/2009 | |
| WO | WO-2009047564 | A2 * | 4/2009 | ............. A61L 15/26 |

* cited by examiner

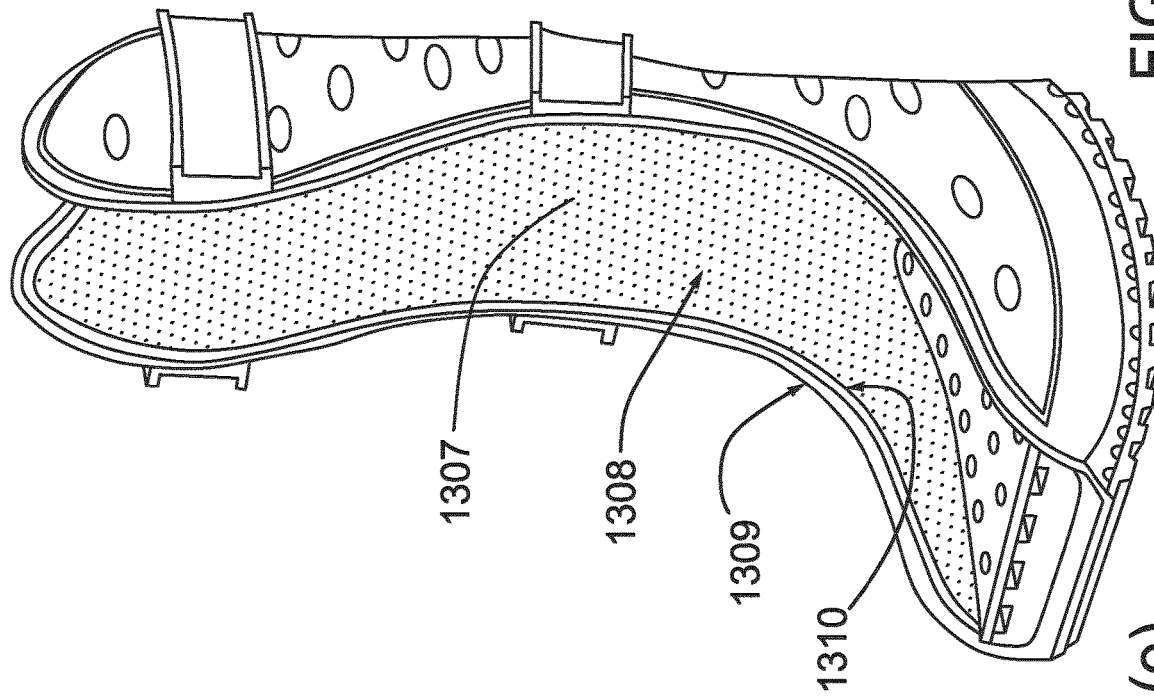
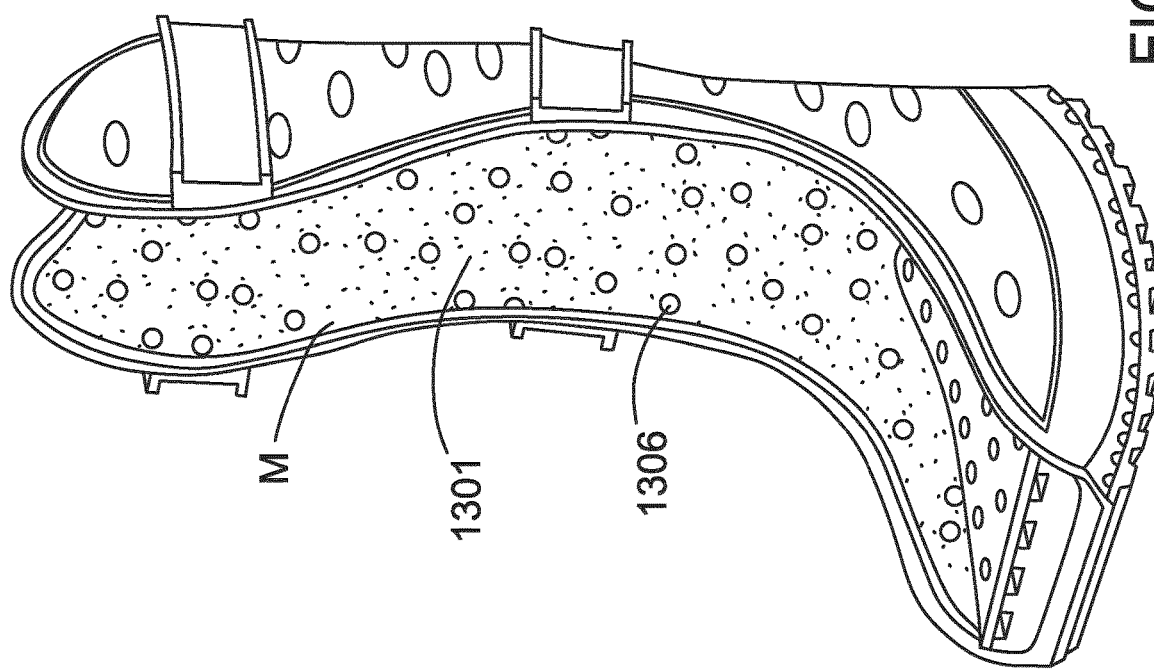

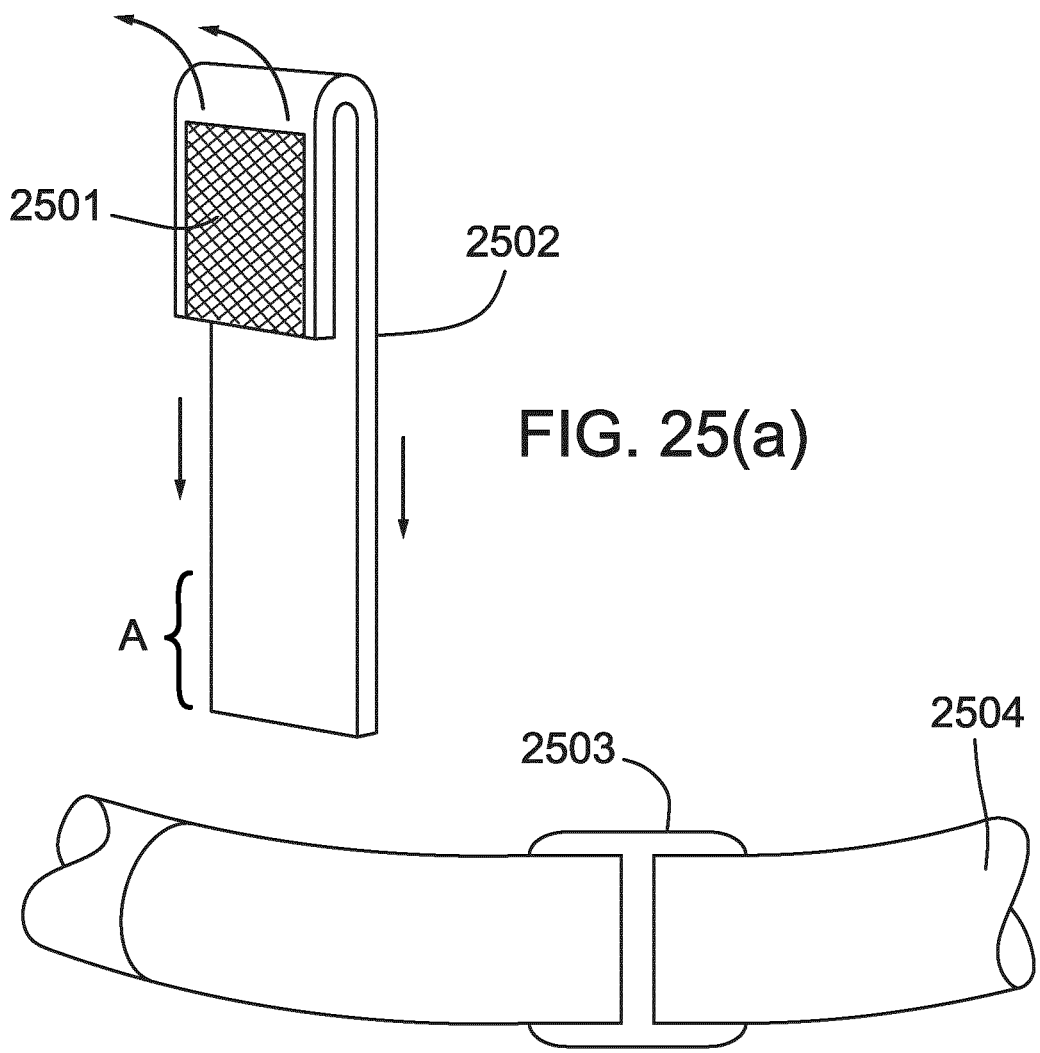
FIG. 25(a)
FIG. 25(b)
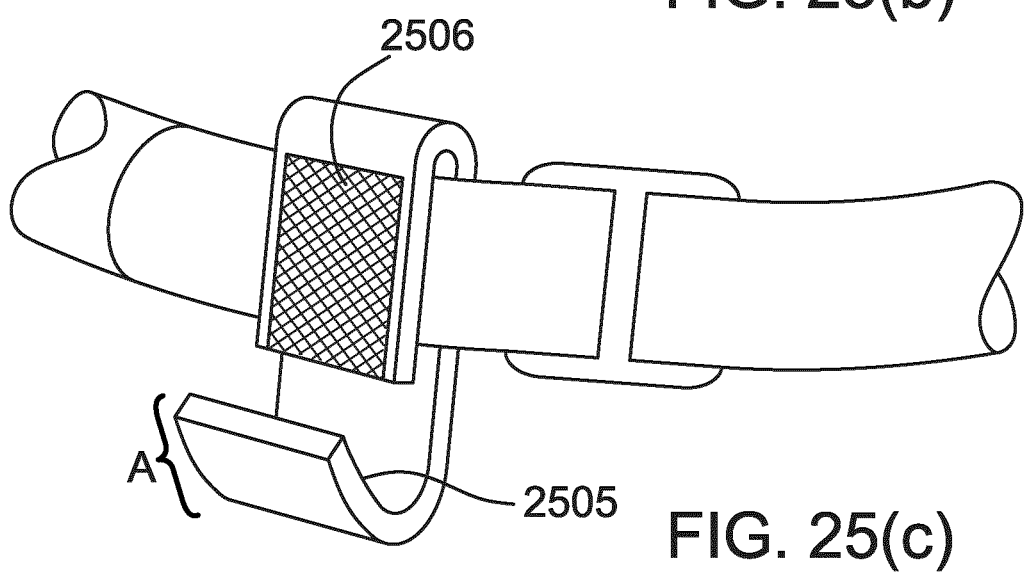
FIG. 25(c)

POROUS ORTHOPEDIC OR PROSTHETIC SUPPORT HAVING REMOVABLE CUSHIONING AND SCAFFOLDING LAYERS

FIELD OF THE INVENTION

The present specification relates generally to orthopedic and prosthetic supports and more specifically relates to orthopedic and prosthetic supports which are perforated or porous so that air may pass through the orthopedic or prosthetic support in either direction to aerate the area enclosed or covered by the orthopedic or prosthetic support.

BACKGROUND OF THE INVENTION

An orthopedic support is a device used to help with the correction or prevention of deformities, disorders and injuries of the skeleton and associated structures (i.e. tendons and ligaments). Orthopedic supports include such devices commonly referred to as casts, splints and braces, which are designed to immobilize and protect injured limbs or other parts of the anatomy of a human or animal.

Since orthopedic supports often enclose or cover part of the body and are preoccupied with immobilization and protection of the concerned body part, they may fail to allow for much circulation of air to the anatomy that is enclosed or covered by the support. For example, braces made of collapsible foam may flatten when compressed against the wearer and limit the exchange of external air with the wearer's skin. In practice, the wearer of the orthopedic support may find wearing the orthopedic support uncomfortable as the covered area of their anatomy may become too warm causing perspiration. In addition to causing the wearer discomfort, perspiration and lack of adequate aeration over several hours or days may be unhygienic and may increase the likelihood of skin irritation, infection and other undesirable health conditions. Prosthetic supports, used in conjunction with a prosthesis, may have similar deficiencies with respect to providing adequate aeration.

In addition to allowing for aeration to the skin, it would be desirable for orthopedic and prosthetic supports to provide the appropriate amount of cushioning, support and protection at the locations they are needed depending on the individual needs of the wearer which may change over time.

Accordingly, there remains a need for improvements in the art.

SUMMARY OF THE INVENTION

In accordance with an aspect of the invention, there is provided an orthopedic support including at least three layers that allows for aeration and cushioning of the enclosed or covered area of the wearer's anatomy. The wearer may be a human or an animal. The orthopedic support may include an inner cushioning layer which is compressed against the skin or surface of the body in use. An intermediate scaffolding layer may be situated substantially parallel to the inner cushioning layer and may be maintained in spaced apart relationship with the inner cushioning layer by spacer members. An exterior layer may overlay the intermediate scaffolding layer and may be either a flexible breathable fabric such as velvet or a thermoplastic substance with a plurality of perforations. The inner cushioning layer and the intermediate scaffolding layer may include a plurality of perforations providing air pathways through the layers. The grid-like arrangement of spacer members may also define air passages between the inner and intermediate layers which may further enhance the permissible circulation of atmospheric or exterior air surrounding the orthopedic support to the skin area enclosed or covered by the orthopedic support.

In accordance with a further aspect of the invention, there is provided a prosthetic support for use with a prosthetic, such as a prosthetic limb. The prosthetic support may be placed around the wearer's limb and in between the prosthetic and the wearer and comprises at least three layers that allows for aeration and cushioning of the enclosed or covered area of the wearer's anatomy. Such a support may be made according to the same or similar configurations of layers and other components as the various embodiments of orthopedic supports described herein with appropriate modifications in the shape and size of the support and the placement of one or more securing mechanisms.

According to an embodiment of the invention, there is provided an orthopedic or prosthetic support comprising: a substantially porous inner layer comprising a flexible cushioning material including a plurality of perforations extending between opposite sides of the layer; a substantially porous intermediate layer comprising a flexible material including a plurality of perforations extending between opposite sides of the layer and a plurality of spacer members arranged in a repeating pattern, wherein the substantially porous intermediate layer is situated substantially parallel to the substantially porous inner layer yet spaced apart by the spacer members so as to provide air passages between the intermediate layer and the inner layer and air pathways through both the plurality of perforations in the intermediate layer and the plurality of perforations in the inner layer and wherein the flexible material of the intermediate layer has greater hardness than the flexible cushioning material of the inner layer; a substantially porous exterior layer enclosing the intermediate layer, wherein air external to the orthopedic support may pass through the substantially porous exterior layer to the air pathways; and a securing mechanism affixed to at least the exterior layer for securing the orthopedic or prosthetic support to a living being.

Other aspects and features according to the present application will become apparent to those ordinarily skilled in the art upon review of the following description of embodiments of the invention in conjunction with the accompanying figures.

BRIEF DESCRIPTION OF THE DRAWINGS

Reference will now be made to the accompanying drawings which show, by way of example only, embodiments of the invention, and how they may be carried into effect, and in which:

FIGS. 13(a)-(h) show a perspective view of a walking brace according to an embodiment of the invention after successive steps during assembly;

FIGS. 25(a)-(d) shows a securing mechanism for an orthopedic support according to an embodiment of the invention;

Like reference numerals indicate like or corresponding elements in the drawings.

DETAILED DESCRIPTION OF THE EMBODIMENTS

According to aspects of the invention, orthopedic supports may be provided which include configurations of substantially porous cushioning and scaffolding layers. Such orthopedic supports may be used, without limitation of the generality of the foregoing, as wrist braces, forearm braces, elbow braces, heel braces, or walking braces, as well as in an orthopedic immobilizing cast. The configurations of substantially porous cushioning and scaffolding layers may also be used as an orthopedic support in mattresses, wheelchairs, chairs, seats, and shoes, in order to provide both cushioning close to the skin or surface of the wearer's body and greater support and protection further away from the skin or surface of the wearer's body, and all the while allowing for adequate aeration of the enclosed or covered area of the wearer's body.

According to a further aspect of the invention, a prosthetic support including similar configurations of substantially porous cushioning and scaffolding layers may be used with a prosthetic, such as a prosthetic limb, wherein the layers may be placed in between the prostheses and the wearer so as to reduce or prevent inflammation of the part of wearer's limb that would otherwise abut against the prosthesis. Such a prosthetic support may be made according to the same or similar configurations of layers and other components for the various embodiments of orthopedic supports described herein with appropriate variations in the shape and size of the support and the securing mechanism, as would be appreciated by a person skilled in the art.

According to certain aspects of the invention, air bladders may also be provided to provide compression and immobilization in combination with the porous cushioning and scaffolding layers. The porous cushioning and scaffolding layers may be removable and may come in versions of different hardness so that the wearer can replace one or both layers for a one of a different hardness or for hygienic reasons such as washing or laundering the layer as desired. The porous components of the orthopedic or prosthetic support may allow the wearer to wear the orthopedic prosthetic support for several hours or even days with no or reduced perspiration since external air may better reach the enclosed or covered area of the wearer's body despite the cushioning layer being compressed tightly against the wearer.

Figure 1:
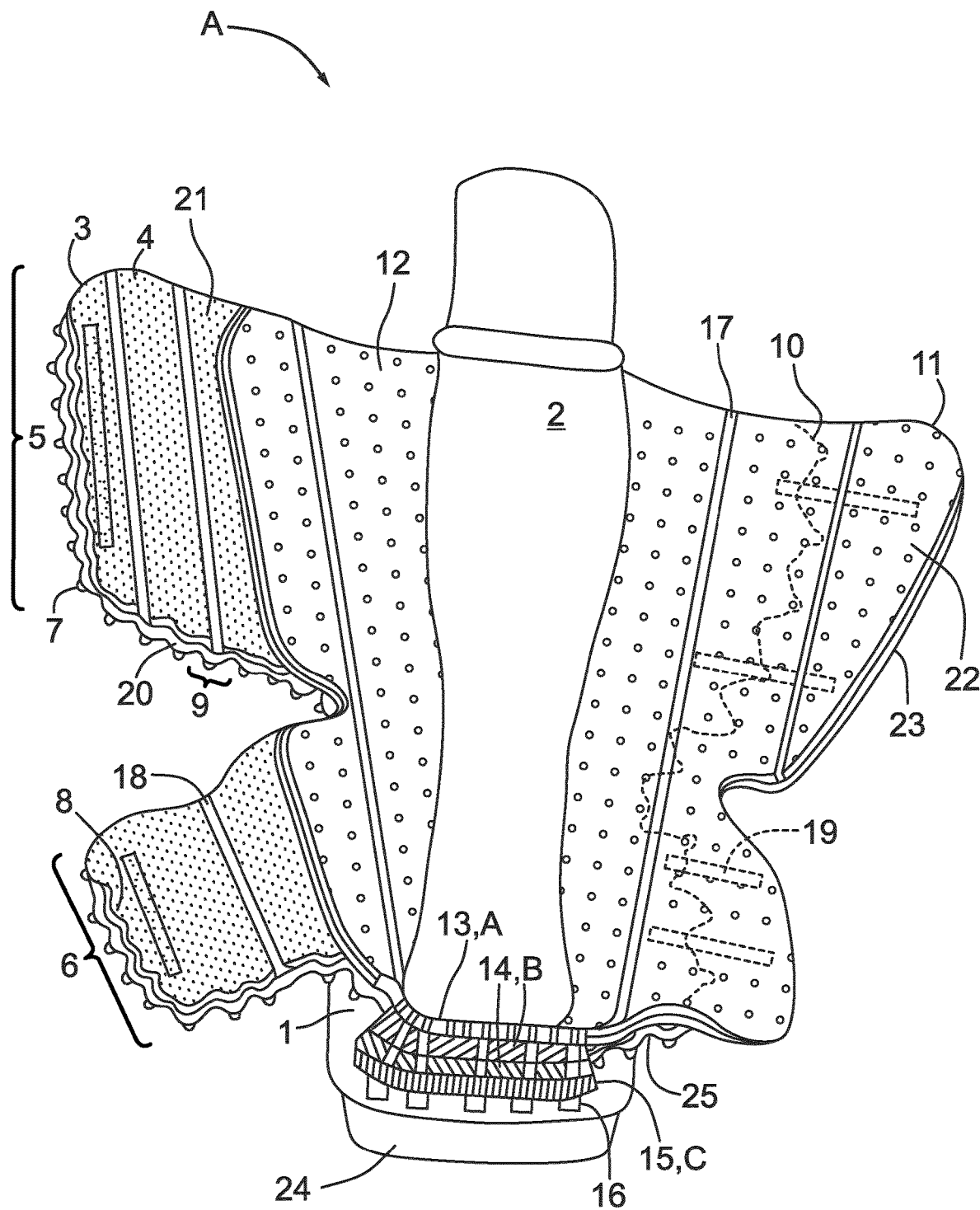
FIG. 1 is a front view of a walking brace in an open position according to an embodiment of the invention.

According to an embodiment as shown in FIG. 1, a porous dual pad A may be contained inside a walking brace 1. The wearer's leg may be covered by a porous sock 2, such as a cotton sock, and lie inside pad A. According to an embodiment, pad A may comprise two layers, an intermediate layer 3 and an inner layer 11, which each may be made of an elastomeric material such as thermoformable ethylene-vinyl acetate (EVA) which may have hypoallergenic properties, or silicone or polyurethane materials. According a further embodiment, a combination of materials may be used, such as silicone membranes with gel membranes or with EVA or polyethylene membranes as well. The two layers 3 and 11 may be made manufactured by molding procedures, or by extrusion or thermoforming. Layers 3 and 11 may have perforations or holes 4 and 12. The holes may be of any diameter and spaced apart by any suitable distance to allow a sufficient amount of external air to circulate to the wearer's anatomy. The layers 3 and 11 may be contoured to the shape of the wearer's body part, which in the example shown in FIG. 1 may be to the shape of the exterior of a human calf and around the contour of a plantar fascia. The intermediate layer 3 may include spacer members such as domes or protrusions 9 on its outer side. Protrusions 9 may be separated from each other by channels or grooves 25.

On the top of protrusions 9 may be bumps 7 and the previously mentioned holes 4 may surround protrusions 9. According to an embodiment, the intermediate layer 3 may be of dual hardness (i.e. two different hardnesses) and may include an outer layer 20 which may be of durometer 50 and an inner layer 21 which may be of durometer 20. Because of its high durometer, the outer layer 20 may help the layers to avoid collapse when pad A is compressed against the walls of the walking brace 1 during use.

According to an embodiment, the inner layer 11 may be of dual hardness as well. It may have an inner cushioning layer 22 of hardness 8 and an outer layer 23 of hardness 20, which may be the same as the opposite inner layer 21 of the intermediate layer 3. According to an embodiment, the layer 11 may be made of a hypo-allergenic foam and may be soft and porous. The combination of low hardness and softness of the material may provide comfort to the wearer. This embodiment may therefore provide comfort through the soft inner layer 11 and at the same time provide a harder scaffolding layer 3 which allows for circulation of external air to the enclosed or covered portion of the wearer's body through and between the layers 11 and 3.

Figure 16:
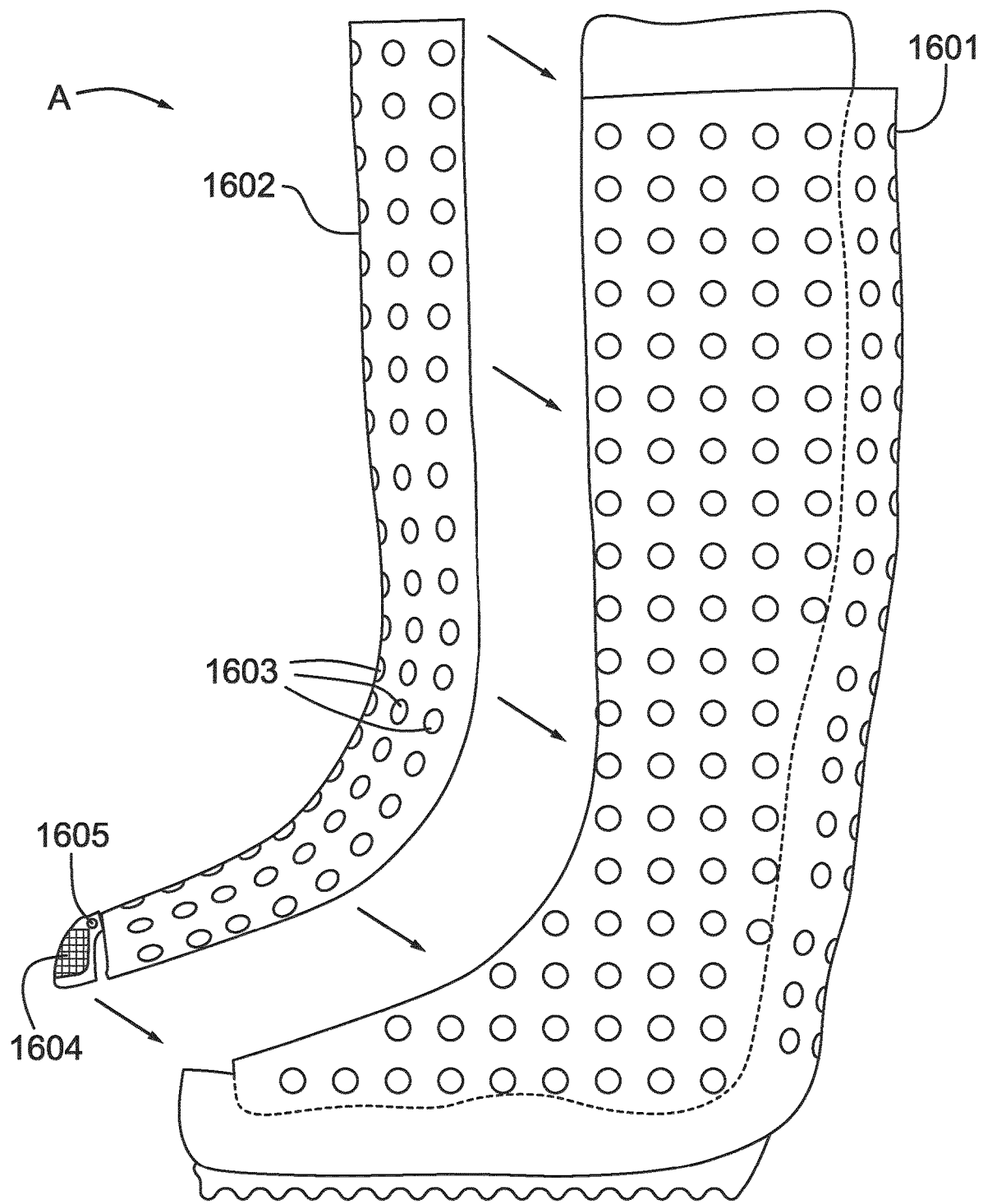
FIG. 16 is a partially exploded side view of a walking brace according to an embodiment of the invention showing a front panel or shield removed and shown relative to a wearer's lower leg.
Figure 17:
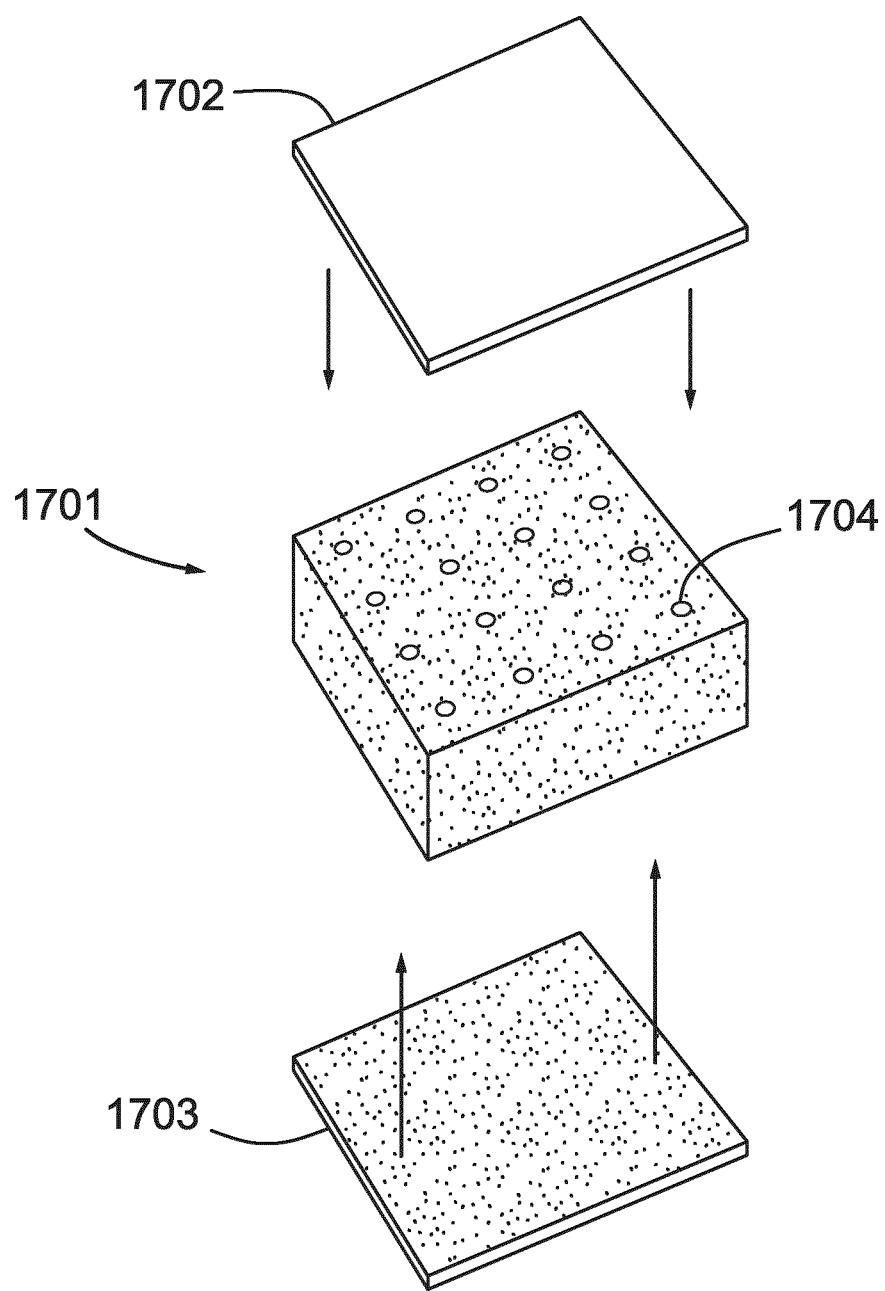
FIG. 17 is an exploded view of a sheet of hypoallergenic foam laminated by fabric on each side according to an embodiment of the invention.

The inner layer 11 may be covered by a fabric with small holes such as mesh net as shown in FIG. 13. According to an embodiment, the layers 3 and 11 may be laminated by porous fabrics on one side or both sides. According to an embodiment, the walking brace 1 may be laminated externally by an external fabric such as velvet. The walking brace may also comprise a front cover as shown in FIGS. 16 and 17 that covers the front of the leg.

As indicated by example above, the hardness of the various layers is configurable and therefore a suitable configuration of cushioning and support may be provided according to the wearer's present needs. When selecting the hardness for the various layers discussed herein, a low hardness may be more suitable where the layer is covering an injured body part or a sensitive surface of the body. Alternatively, where a layer is pressed against hard surface of the wearer's anatomy, the layer may be made of a higher hardness.

It should be appreciated that although a walking brace is illustrated in FIG. 1 and many of the other figures, it is also possible to employ an orthopedic support constructed in accordance with embodiments of the invention which is not a walking brace and may be adapted for use on a body part other than the lower leg. Moreover, although the illustrated walking brace is adapted for use on the lower leg of a human, it will be appreciated by those skilled in the art that a brace constructed in accordance with embodiments of the invention may also be used on an animal's body part.

To assemble the embodiment as shown in FIG. 1, the overlapping side covers 5 and overlapping foot covers 6 may be bent toward each other and around the front parts of the leg and towards the superior part of the foot with little in the way of resistance because the layers 3 and 11 may include longitudinal channels 17 which may act as hinges. This may allow the membranes or layers of pad A to bend more easily when the walking brace 1 is closed, which may allow the walking brace 1 to be closed faster and more easily as well as potentially offer more comfort to the wearer.

The walking brace 1 may be closed by overlapping the overlapping side covers 5 and overlapping foot covers 6 on top of each other at any desired position. According to an embodiment shown, Velcro™ strips 18 may be sewed vertically inside layer 3 and Velcro™ strips 19 may be horizontally sewed on the outside of layer 11. The surface that lies under each of Velcro™ strip 18 and 19 may be flat for a strong sewing. This cross-lock fastening may allow for a quick fastening of the orthopedic support for various diameters and sizes of limbs.

According to an embodiment as shown in FIG. 1, layer 3 may be wider/longer at the left side of the leg than layer 11 and narrower/shorter at the right side of the leg than layer 11 as denoted by hidden vertical edge 10 of layer 3. By having layer 11 not fully placed under layer 3, the walking brace 1 may have two layers instead of four layers locked around the front part of the leg when the walking brace 1 is assembled to enclose the lower leg and therefore the brace is not double the thickness around the front part of leg.

Pad A may provide for the circulation of external air to the wearer's body part enclosed or covered by the orthopedic support via the holes 4 and via the holes 12. The holes 4 and 12 do not have to be aligned (but could be) in order to let air flow reach the wearer's body as holes 4 are not obstructed by layer 11. As the holes 4 may lie on curved surfaces, there may be empty spaces between layers 3 and 11 allowing air to circulate and collect especially within the cavities 8 formed under spacer members such as protrusions 9. The protrusions 9 may be arranged in a substantially repeating pattern such as a grid-like repeating pattern as shown.

According to an embodiment as shown in FIG. 1, holes 4 may have a diameter of about 0.5 mm up to about 2 mm. Other diameters might be also appropriate with consideration given to the thickness of the material and the distance between holes 4 so that adequate aeration may be realized while maintaining sufficient stability for layer 3. The holes 4 may surround the bumps 7. According to an embodiment, holes 4 are not placed on the bumps 7 so as to preserve bumps 7 as solid.

According to an embodiment, holes 12 on layer 11 may be of a diameter of about 0.5 mm to about 5 mm. These holes may be close to each other, being separated by about 2 mm. The closer together the holes are, the greater the aeration will be to the wearer's skin but an increasing density of holes may also reduce the support and protection provided by layer 11. Therefore, as will be appreciated by a skilled person, the characteristics of the holes should be selected in view of a several factors including the thickness and the hardness of the layers and the desired amount of airflow.

According to an embodiment, layer 11 may be of a thickness of about 3 mm to about 5 mm. By selecting the appropriate hardness and thickness, holes 12 may remain open when layer 11 is compressed such as when the support is installed against the wearer's body using a securing mechanism such as Velcro™ belts or when the air bladders (described further below) are inflated or both. The continued exchange of airflow may reduce sweat, odor and itchiness, and may accordingly lead to a shorter and improved rehabilitation period.

According to an embodiment, bumps 7 may be in contact with the internal walls of the walking brace 1. External air may enter inside the walking brace 1 from around the perimeter of the brace 1 and may surround the bumps 7. External air may enter inside the walking brace 1 through the openings present on the walls of the walking brace 1. The external air may flow between layer 3 and layer 11 and towards the empty space inside the cavities 8 and then through the holes 12 of layer 11 and then to the wearer's covered or enclosed body part. The cavities 8 may therefore act as a temporary reservoir of air.

External air may also enter the brace from the frontal openings or grooves 16, which may include interconnected grooved channels incorporated in the bottom of the walking brace 1. External air may then travel upwards from the channels or grooves 16 and go through the holes of the mesh net sole 15.C, then flow further upwards and through the holes of the dual hardness sole 14.B, and then reach the surface of the plantar fascia of the wearer's foot. According to an embodiment, the mesh net sole 15.C may include small holes that may be close to each other for ample aeration. The mesh net sole 15.C may be of a high durometer such as 50, so that it may be capable of withstanding substantial forces without sinking between the grooves 16. Also shown is an external interchangeable rubber base 24 which may be included according to an embodiment.

Figure 4:
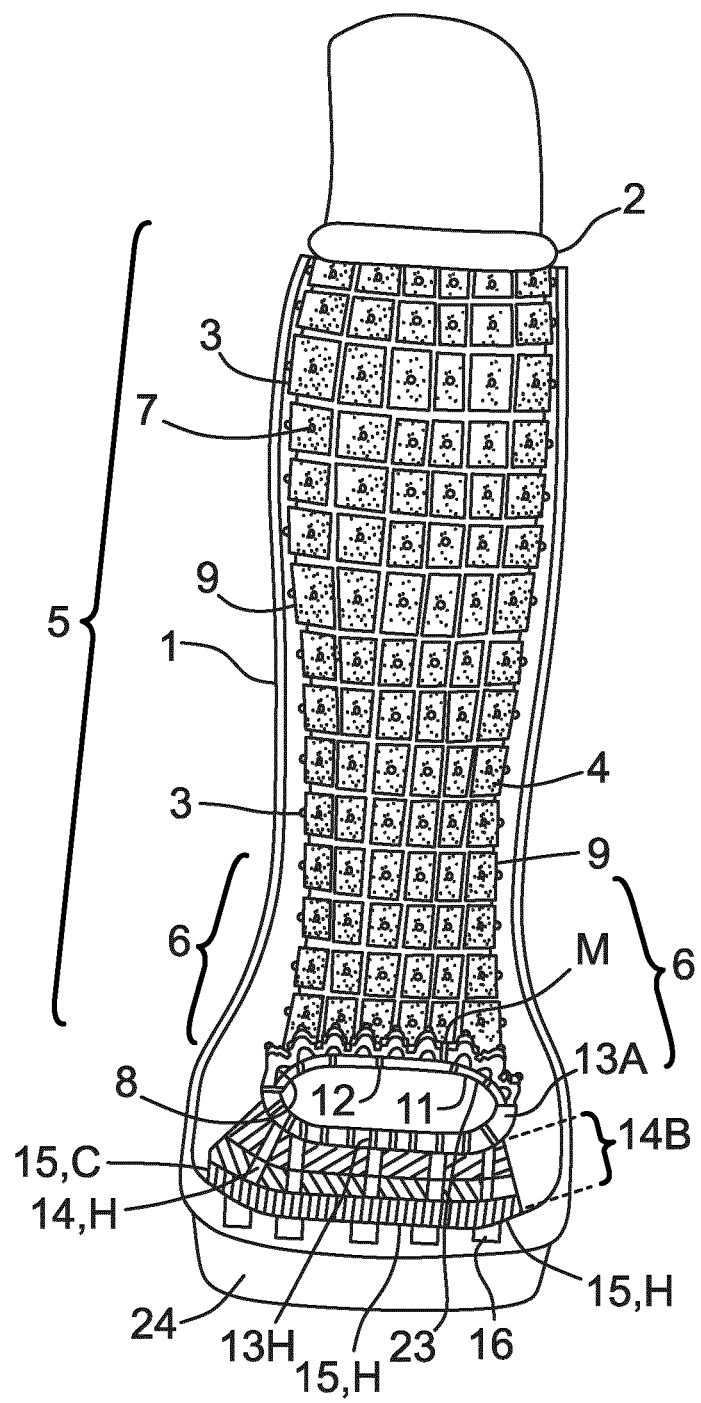
FIG. 4 is a front view of the walking brace shown in FIG. 1 in a fully-assembled position.

According to an embodiment as shown in FIG. 1, plantar fascia cushion or pad 13.A may be a cushion made of EVA and including holes 13.H as shown in FIG. 4 and may be sewed to the walls of pad 11. Pad 13.A and layer 11 may be connected together via stiches or adhesives or Velcro™ at different spots around the posterior parts around the calf and Achilles area.

According to an embodiment, the pad 13.A may be made of two layers of different hardnesses where the outer layer is harder than the inner layer closer to the wearer's foot. The lower layer may face the mesh net sole 15.C and may have a hardness of durometer 50 which may be strong enough to offer an additional support to the wearer so that he or she does not sink in between the channels 16. The upper layer may be softer and may have a hardness of durometer 20. This configuration may help the plantar fascia as may provide a comfortable and non-collapsible supporting area.

Figure 2:
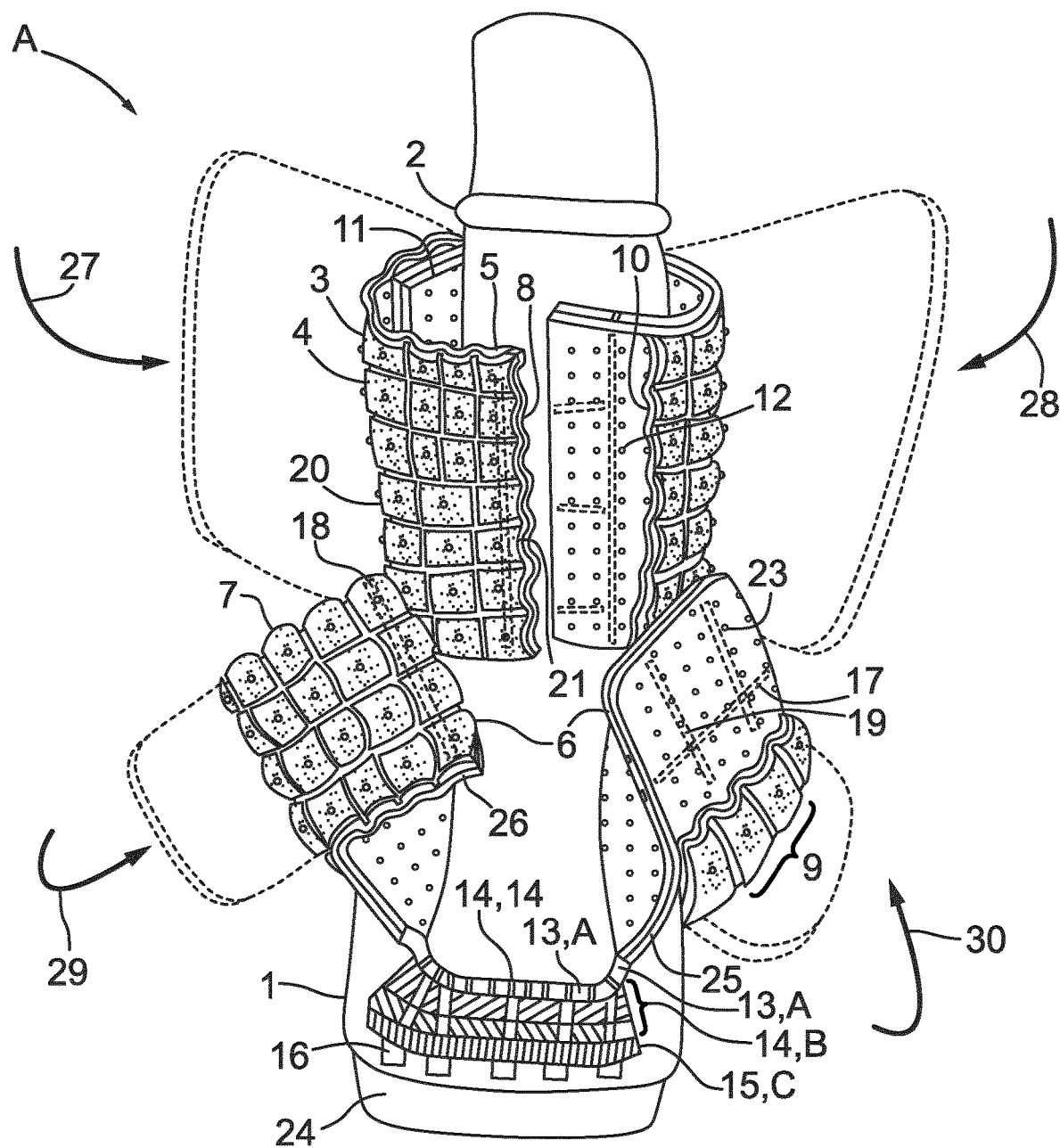
FIG. 2 is a front view of the walking brace shown in FIG. 1 in a partially-assembled position.

FIG. 2 shows walking brace 1 of FIG. 1 in the process of being wrapped around the wearer's leg as indicated by arrows 27 and 28 next to overlapping side covers 5. Then the same process is followed for the foot's overlapping foot covers 6 as indicated by arrows 29 and 30. A line of separation 26 between layers 22 and 23 and holes 14.H in dual hardness sole 14.B are also indicated in this figure.

As may be seen according to this embodiment, the overlapping portion of overlapping side cover 5 may be made of only one layer (layer 11 on the right side and layer 3 on the left side). This allows the closed overlapping covers to be only two layers thick as layer 3 is on top of layer 11. This may provide a uniform installation by only having two layers (instead of 4) surrounding the wearer's lower leg and may therefore avoid the brace from getting too thick at the front of the leg and causing overheating.

As shown in FIG. 2, the overlapping side covers 5 may have Velcro™ strips sewed on them. The right-sided side cover 5 may have Velcro™ strip 19 which may be sewed horizontally and separated by a distance of about 5 cm from each other. The left sided side cover may have a Velcro™ strip 18 that is vertically situated inside the vertical cover. This may be described as a cross-locking system and may allow the brace to fit various sizes of leg and to lock quickly. A cross-locking system may also be applied to the overlapping foot covers 6 for the wearer's foot. According to an embodiment, the Velcro™ strips may be sewed inside the layer 3 on top of a flat rectangular surface.

The pad may be contoured towards the parts of the leg through the use of grooves 17 that may act as hinges and may be made using thermoforming techniques. Grooves 17 may be located inside the internal walls of the overlapping side and foot covers 5, 6 on both sides of the leg and foot.

Figure 3:
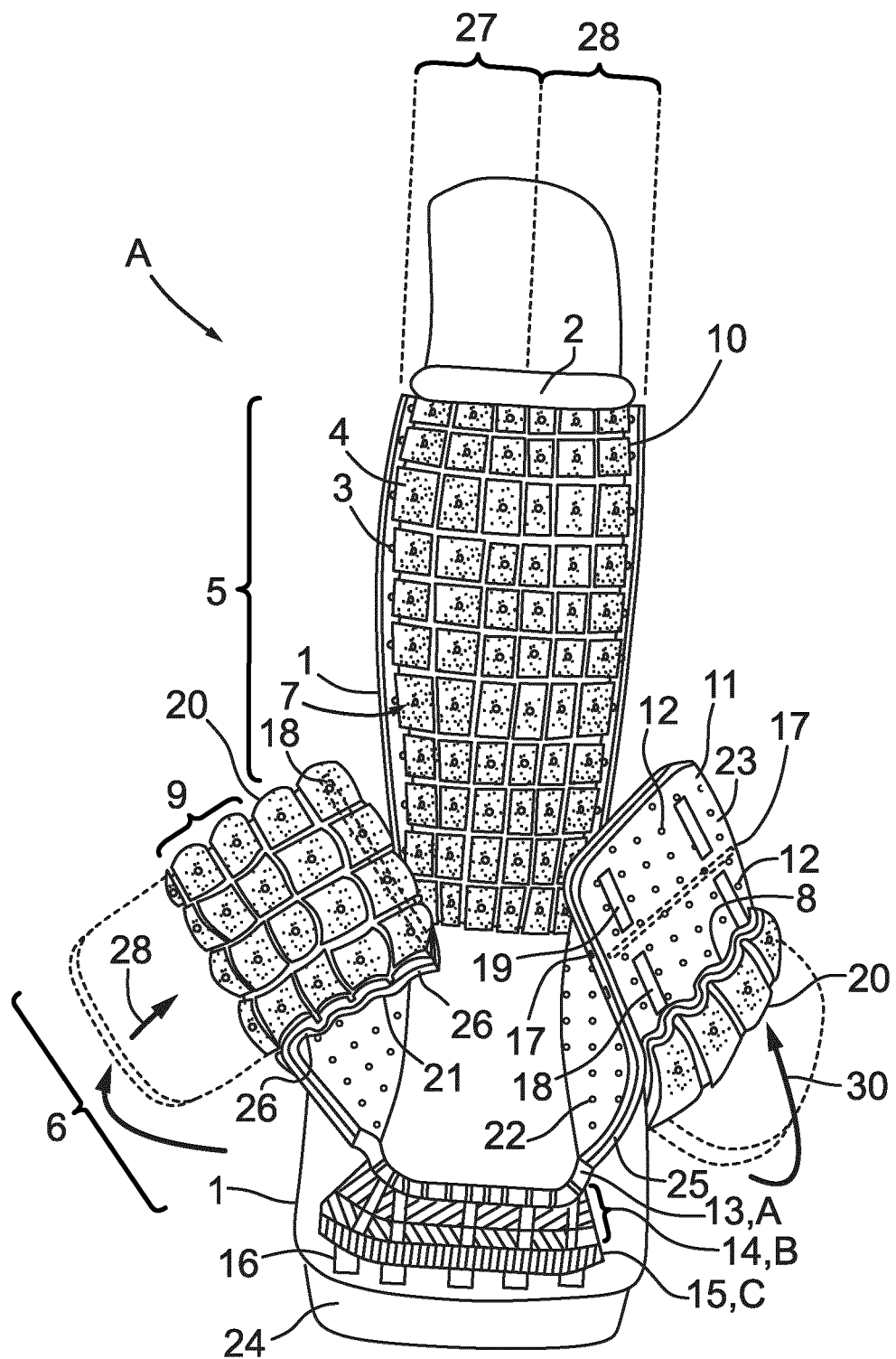
FIG. 3 is a front view of the walking brace shown in FIG. 1 in a mostly-assembled position.

FIG. 3 shows walking brace 1 of FIGS. 1 and 2 where the overlapping side covers 5 are closed around the wearer's leg by way of the Velcro™ strips. Arrows 29 and 30 indicate the direction for closing overlapping foot covers 6.

FIG. 4 shows walking brace 1 of FIGS. 1 to 3 where overlapping side covers 5 are closed around the wearer's leg and overlapping foot covers 6 are now closed around the wearer's foot as well.

Figure 5:
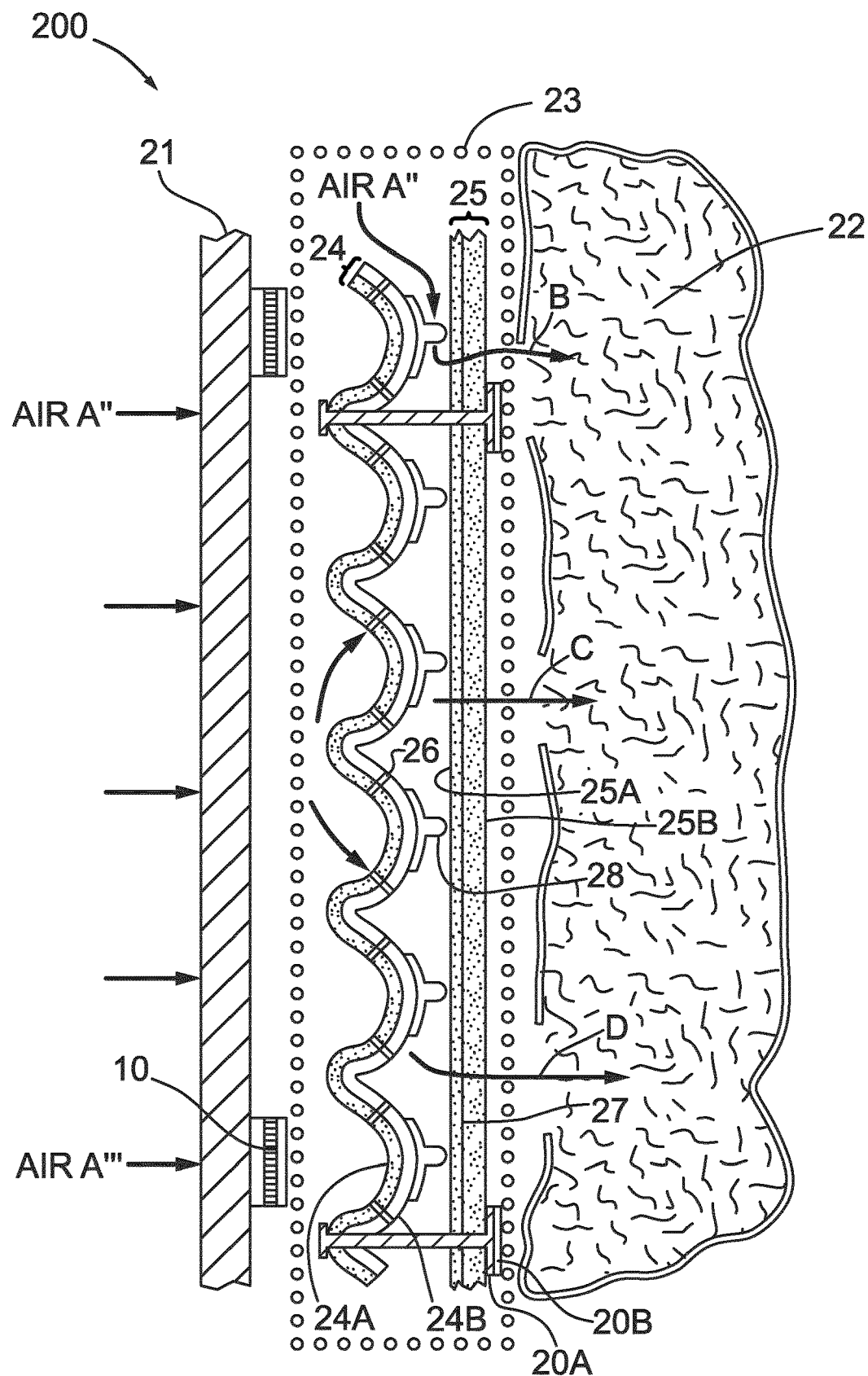
FIG. 5 is a cross-sectional view of an inner layer and an intermediate layer of an orthopedic support according to an embodiment of the invention.

FIG. 5 shows a cross-section of the inner and intermediate layers of an orthopedic support or brace 200 according to an embodiment. The wall 21 of the brace 200 may be made of a soft fabric suitable for use in wrist braces, forearm braces, elbow braces, heel/ankle braces, knee braces, torso braces, neck braces, and the like. According to an embodiment, the soft fabric may be made of one or more of the following: polyurethane, nylon, Spandex, or polyethylene, or any other suitable soft hypoallergenic fabric. Layers 24 and 25 that are inside the brace 200 may be selected to be hard enough to sustain external pressures when the brace 200 is installed tightly around the wearer. Optionally, a thin and rigid piece of plastic or metal may also be inserted behind the wall 21 to provide support for the brace.

Layers 24 and 25 may be inserted inside an enclosing envelope such as tubinette envelope 23 or may be attached to each other by other suitable attachments means such as adhesives or stitches, or both. Tubinette envelope 23 may be made of cotton with pores, or any similar hypoallergenic fabric or fiber, and may be detachable from the brace 200 for washing. Velcro™ attachments 30 may keep the tubinette envelope 23 attached to the wall 21 of the brace 200. The tubinette envelope 23 may envelope a porous membrane including layer 24 which may have domes 29 and layer 25 which may be flat. Domes 29 on layer 24 may be spacer members arranged in a repeating pattern such as a grid-like pattern and may serve to prevent the collapsing of layers 24 and 25 when the layers 24 and 25 are exposed to compressive forces. Domes 29 may also have an internal layer 24.A of about durometer 35 and an outer layer 24.B on top of internal layer 24a of a lesser durometer of about 25. The domes 29 may also have a bump 28 on top of each dome 29. As should be appreciated, the layers move from harder to softer durometers as we approach the wearer's anatomy. According to an embodiment, a soft supporting cushion may be provided in layer 25.B which may have a durometer of about 8 and be situated on top of a harder scaffolding layer 25.A which may have a durometer of about 25. It should be appreciated that the durometers may vary according to the present need of the wearer, although the layer closer to the wearer's skin or other anatomy should be softer and lower in durometer than layers further away from the wearer. Air pathways B, C, and D are shown for the circulation of external air through the perforations in wall 21, layer 24, and layer 25 to the wearer's skin 22.

According to an embodiment, the tubinette envelope 23 may be omitted and instead fasteners such as plastic fasteners 20A may be used to fasten the layers 24 and 25 together as shown in FIG. 5. The plastic fasteners may include pad foam 20B as shown in FIG. 5 so as to present a soft cushioning surface to the wearer's skin. According to a further embodiment, both a tubinette envelope 23 and plastic fasteners 20a may be used.

Figure 6:
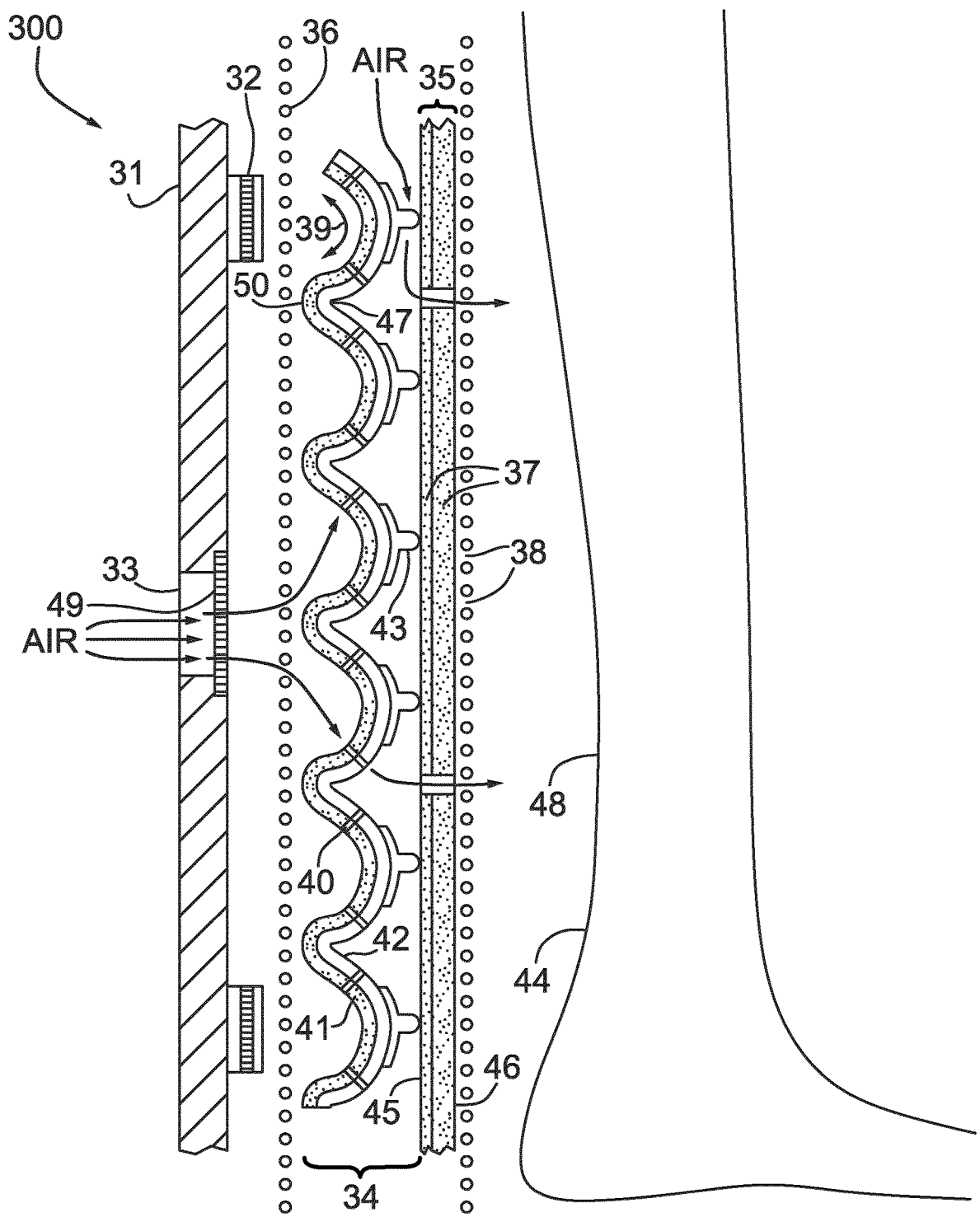
FIG. 6 is a cross-sectional view of an inner layer and an intermediate layer of an orthopedic support according to an embodiment of the invention shown relative to the lower leg of a human.

FIG. 6 shows a further cross-section of the inner and intermediate layers of an orthopedic support or brace 300 according to an embodiment relative to the lower leg 44 of a human on over which there may be a sock 48. Air may pass through openings 33 and mesh net shield 49 of wall 31 which may be attached by Velcro™ strips 32 to tubinette envelope 36. The openings 33 may be shielded from inside by the mesh net shield 19 that may allow external air to enter inside the brace 300 and aerate the wearer's skin. The shield may also prevent the bases 50 and bumps 43 from coming out of openings 33. The shape and dimensions of openings 33 may vary in accordance with the weight of the patient and accordance with the strength of the walls of the brace 300. According to an embodiment, openings 33 may for example be about 40 mm by 40 mm in dimension. Other dimensions for the openings are possible with consideration of the thickness and hardness of the material and the density of openings so as to allow adequate aeration while maintaining adequate stability. Tubinette envelope 36 may enclose layers 34 and 35 and may have pores 38 which may allow air to pass through. Layer 34 may be a protruded membrane of harder layer 41 of about durometer 40 and softer layer 42 of about durometer 30. Layer 34 may have domes 39 between bases 50 and also may have bumps 43 on top of layer 42. Perforations 40 may allow air to pass through layer 34. Layer 35 may be a multiperforated membrane through which air may pass through via pores 37. Layer 35 may include a harder layer 15 of about durometer 30 and a softer layer 16 of about durometer 15. Again, it should be appreciated that the durometers may vary according to the present need of the wearer, although the layer closer to the wearer's skin should be softer and lower in durometer so as to be comfortable to the wearer than layers further away from the wearer which may be better able to sustain force.

According to a further embodiment, layer 34 may be reversed such that the bumps face the wall 31 of the brace and durometers applied to the layers such that the softer layer is closer to the wearer.

Figure 7:
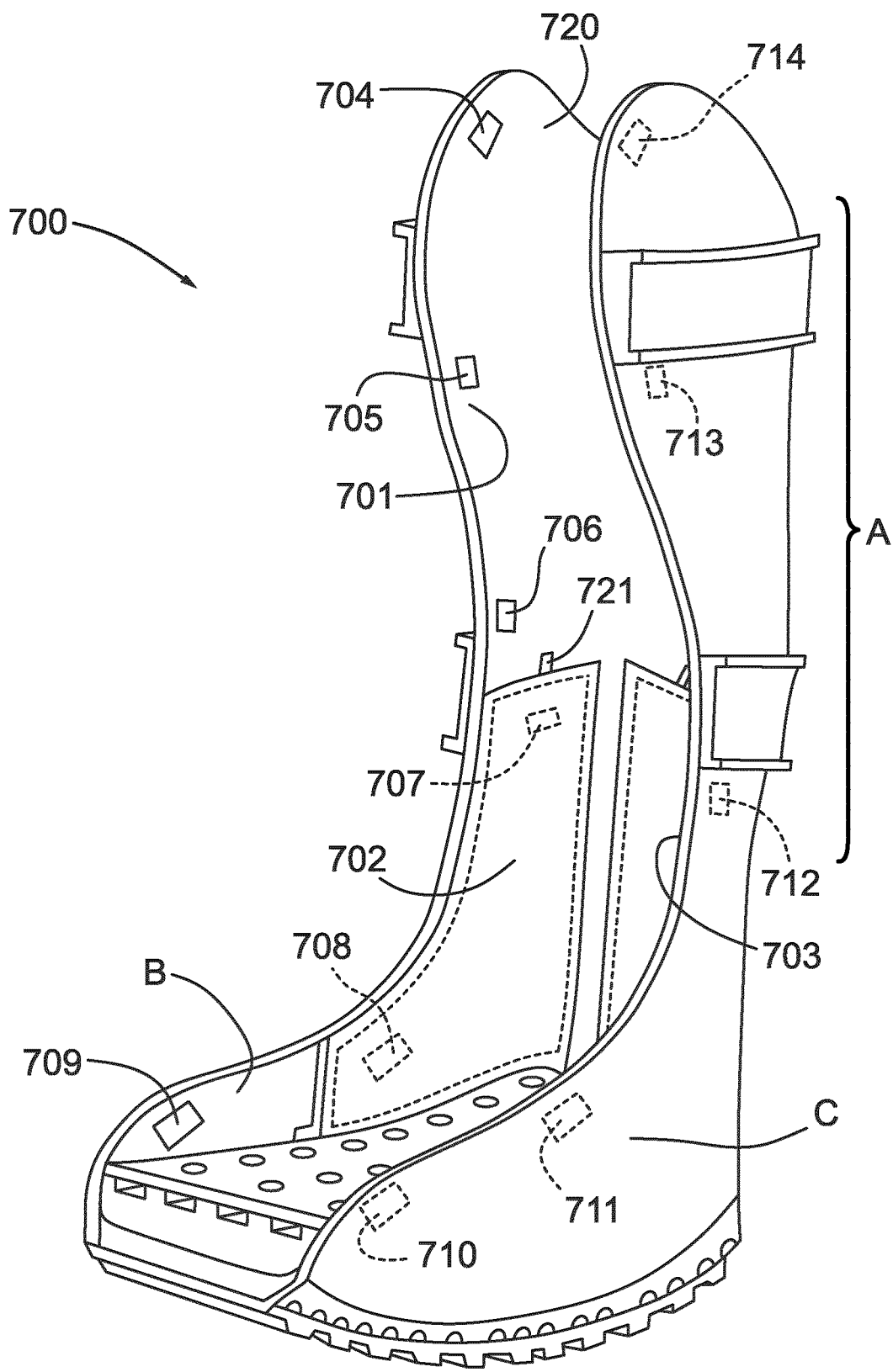
FIG. 7 is a perspective view of a walking brace according to an embodiment of the invention which includes an air bladder.

According to an embodiment as shown in FIG. 7, a pneumatic walking brace 700 is provided. According to the embodiment shown, walking brace 700 may have internal walls which may be configured to house 5 different compartments. Compartment A may cover the calf area, compartments B and C may cover the lateral metatarsal sides, and air bladders 702 and 703 are compartments where the inflation systems may reside.

As shown in FIG. 7, tubes 721 may have valves that supply air to the air bladders 702 and 703. Air bladders 702 and 703 may be fixed to the internal walls 701 of the brace 700 by adhesives or other any other suitable attachment mechanism. Velcro™ strips 704 to 714 may be attached inside the internal walls 701 of the walking brace 700. The Velcro™ strips may be used for the attachment of a plurality of porous cushions over the internal wall 701 of the walking brace 700. According to an embodiment, the walls of the walking brace include a plurality of holes for allowing external air to pass through. It should be appreciated that even without holes through the walls of the brace, external air may be able to enter the brace 700 from around the brace's edges or from around its perimeter.

Compartment A, which may cover the calf area, may be enclosed within an envelope such as tubinette envelope 720, which may be made of cotton with visible pores. Tubinette envelope 720 may be opened and porous cushioning elements may be inserted so as to be enclosed therein. Compartment A may have Velcro™ strips 704, 705, 706, 713, and 714 that may retain the tubinette envelope 720 to the internal wall 701 of the brace 700.

Air bladders 702 and 703 may also be enclosed by tubinette envelopes 720. The tubinette envelopes 720 may be installed firmly against the internal walls via the Velcro™ strips 707, 708, 711 and 712. When air is inserted via tubes 721 into the air bladders 702 and 703, the air bladders 702 and 703 may become compressed against the wearer's anatomy. By attaching each air bladder 702 and 703 independently to the internal walls 701 of the brace 700, they may independently expand or retract without displacing the tubinette envelopes 720.

According to an embodiment, a tubinette envelope 720 may be omitted and the membranes or layers may instead be attached via plastic fasteners such as rivets comprising a male adjustable first portion and a female second portion. Such rivets may be coated with a soft rounded piece made of a gel or EVA material or any equivalent hypo-allergenic material so as to protect the wearer's skin or other anatomy.

According to a further embodiment, air bladders 702 and 703 may be substituted with a single air bladder that may cover the whole internal area of the brace 700. By having a single bladder that may cover all the internal walls of the brace 700, a larger walking brace 700 may be used that may more readily adapt to limbs of various sizes. Furthermore, by using a single bladder, the compression therapy may be uniform around the wearer's anatomy, which may allow for an even distribution of blood flow.

Figure 8:
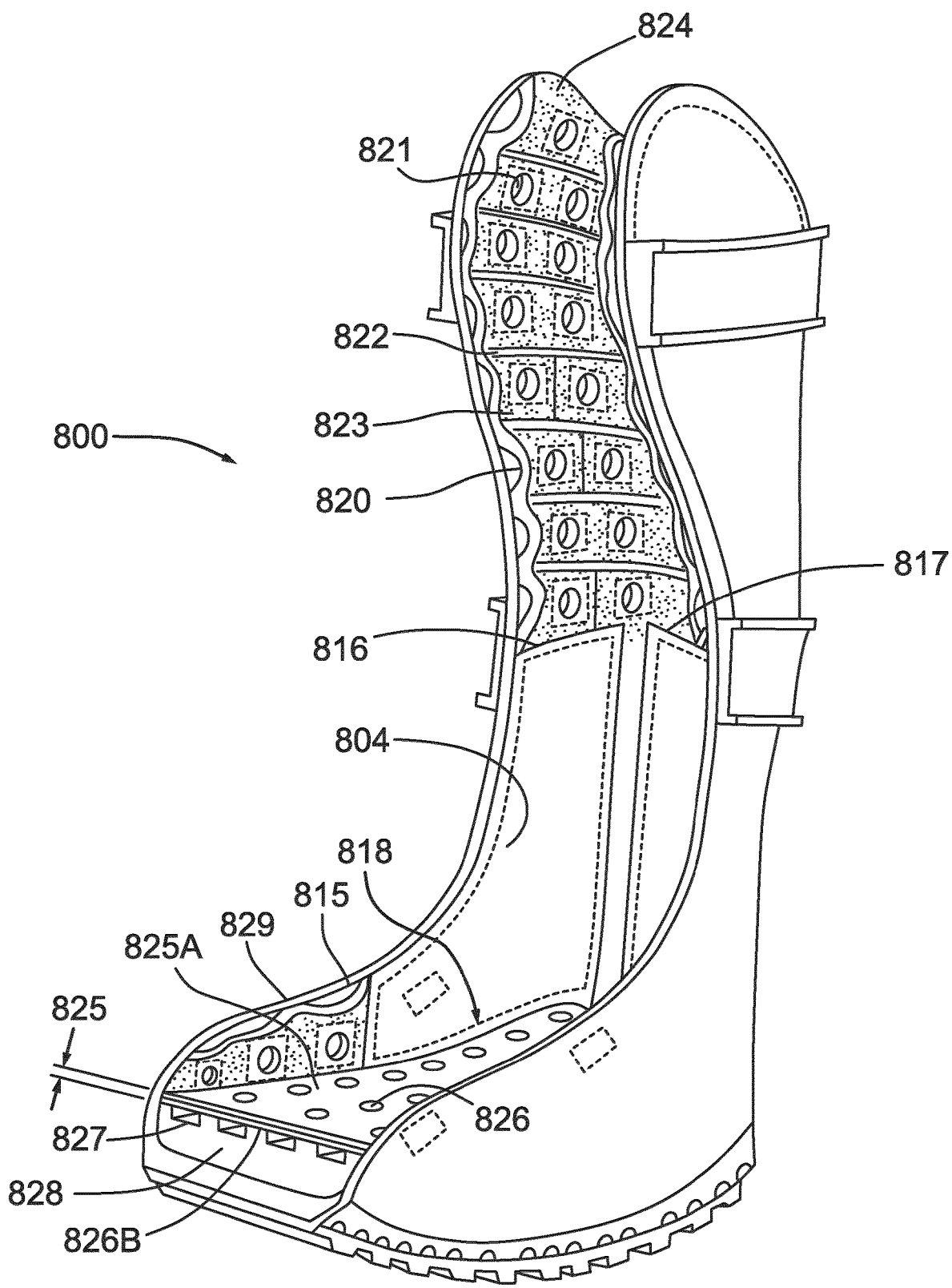
FIG. 8 is a perspective view of a walking brace according to an embodiment of the invention which includes an air bladder and a tubinette envelope.

According to an embodiment as shown in FIG. 8, each tubinette envelope (covering the calf area A and the lateral sides B and C as shown in FIG. 13) may be hollow and may enclose a layer 824 of EVA including a plurality of spacer members such as domes thereon. A first side of the layer 824 may have domes and on top of each dome may be a bump. The domes 820 may face the internal walls 801 of the brace 800. In between the protrusions 821 are grooves 822. The grooves 822 make the layer 824 more flexible and therefore easier to position inside the internal walls 801 of the brace 800. The layer 824 may have holes 823 of about 0.5 mm in diameter. The diameters of the holes may vary depending on how close each hole is to adjacent holes as well as the hardness and thickness of the layer 824. The characteristics of the holes 823 should be such that the layer's domes and bumps do not collapse when the brace is in use. The layer 824 may be assembled on top of the lateral sides 829 and 830 of the brace.

As shown in FIG. 8, there may be an internal sole 825 which may rest on top of a base plate 828. Internal sole 825 may include a plurality of holes 826. The base plate 828 may have channels 827 which may allow air to flow there through. Internal sole 825 may comprise a top layer 825.A that may support the plantar fascia of the foot and a bottom layer 825.B that may be located between the top layer 825.A and the base plate 828. The bottom layer 825.B may be hard enough so as not to sink inside the channels 827 when the wearer applies the walking brace 800. The top layer 825.A may be soft enough to provide a comfortable cushion for the body part. According to an embodiment, the durometer and thickness of the top layer 825.A may be chosen with consideration to the wearer's bodyweight. According to a further embodiment, sole 825 may be a single layer of a relatively hard durometer.

According to an embodiment, the base plate 828 may be interchangeable between a light base plate and a heavy base plate. The light base plate may be made of cork and may be used if the wearer is injured severely enough that he or she cannot lift his or her leg easily from the floor. The heavy base plate may be made of steel and may be used when the wearer needs to rehabilitate the muscles of his or her leg. Accordingly, the base plate 828 and internal sole 825 of dual hardness may help improve recovery of the wearer.

Figure 9:
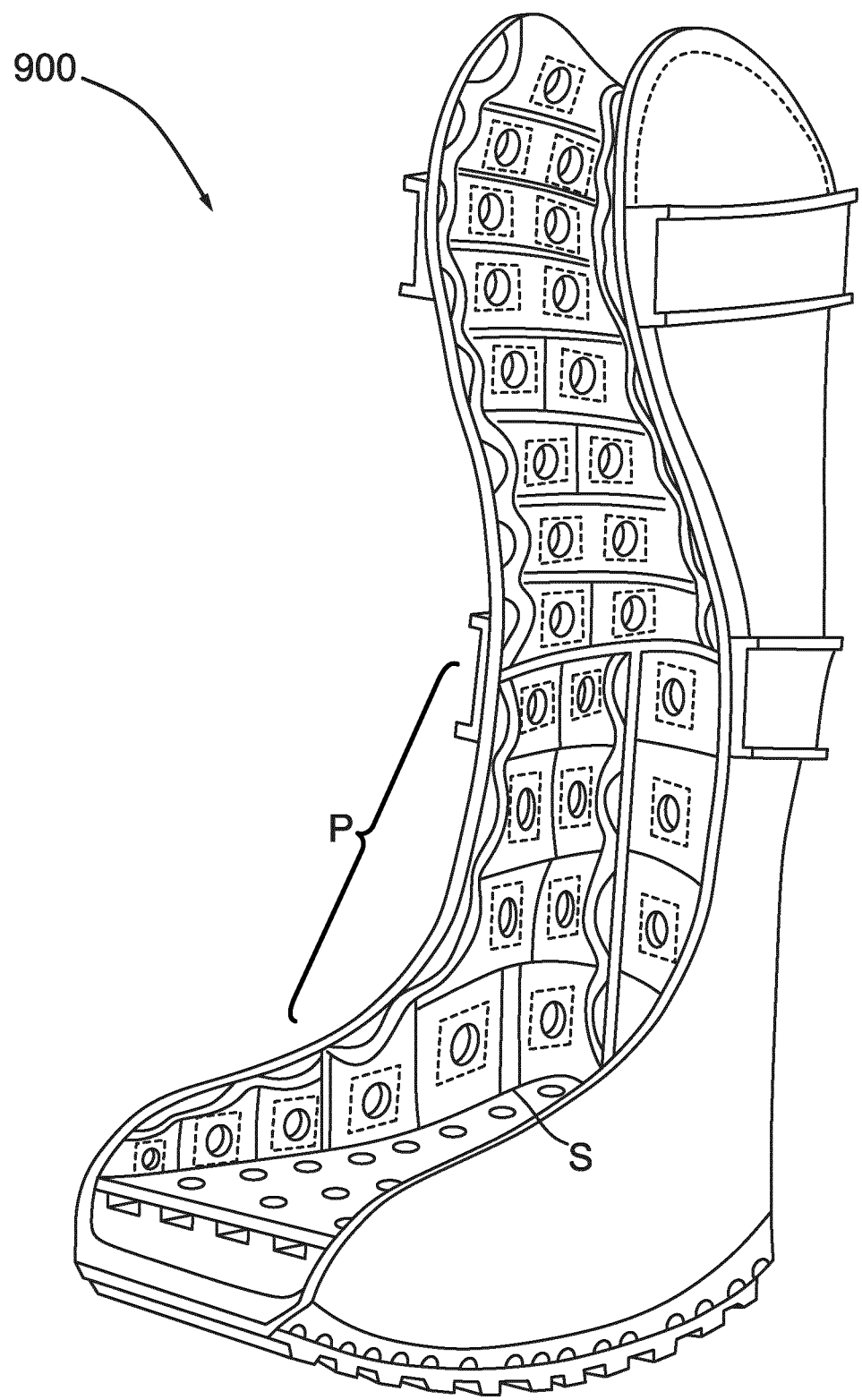
FIG. 9 is a perspective view of a walking brace according to an embodiment of the invention which includes an air bladder and an intermediate scaffolding layer inside of a tubinette envelope.

As also shown in FIG. 8, layer 824 may be installed on top of air bladders 703 and 704 from FIG. 7 (tubinette envelope 804 and not shown on the opposite side in FIG. 8). Air bladders 703 and 704 when inflated with air may have the tendency to push the internal sole 825 away from its original position. To counteract this, a small gap S may be provided as shown in FIG. 9 that may keep the air bladders 703 and 704 away from the internal sole's edge. According to an embodiment, air bladders 703 and 704 may be situated above the surface of the internal sole 25 leaving a spaced gap of at least about 1.5 cm as shown. 815, 816, 817, and 818 may denote "V" openings and 829 denotes a lateral side.

Figure 10:
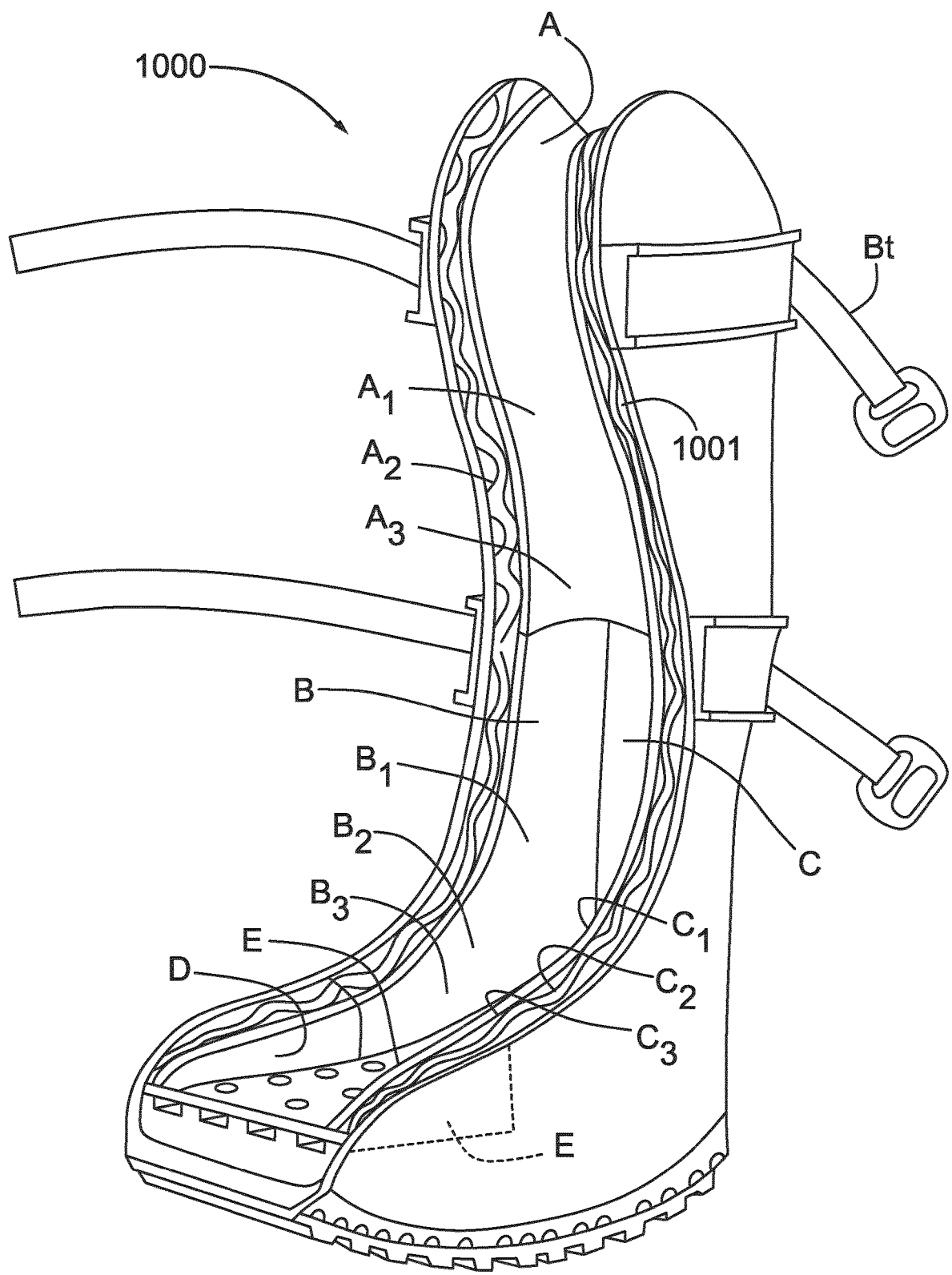
FIG. 10 is a perspective view of a walking brace according to an embodiment of the invention which includes an air bladder, an intermediate scaffolding layer and an inner cushioning layer inside of a tubinette envelope.

According to an embodiment as shown in FIG. 10, a walking brace 1000 may have five air bladders or porous cushions A, B, C, D, and E. The porous cushions may be soft and may allow external air to reach the wearer's skin. Cushion A may cover the calf and surrounding areas. The cushion may include an envelope such as tubinette envelope A1, which may be made of cotton and include pores to allow for the passage of external air from the edges of the brace's walls to the wearer's skin. Inside tubinette envelope A1, there may be a layer A3 and a layer A2. The layers A3 and A2 may be thermoformed to contour to the shape of the calf. The layer A3 may have spacer members such as domes facing the internal walls of the brace 1000. As shown in FIG. 10, the layer A3 may be a mono-layered membrane.

According to a further embodiment, the layer A3 may have a dual durometer where there are two layers therein that may have different durometers with the harder layer facing the internal walls 1001 of the walking brace 1000 and the softer layer facing layer A2. The softer layer provides more comfort to the wearer and the harder outer layer may provide greater support and protection. The harder outer layer may also prevent the domes from collapsing when the brace is compressed against the wearer's anatomy. For instance, the front panel that may keep the brace in place via Velcro™ strips or belts may squeeze the front panel against the shin or front of the leg and such squeezing may put pressure on the domes. The harder, higher durometer layer may therefore reduce the likelihood of or entirely prevent damage to the domes during use of the walking brace.

According to an embodiment, layer A2 may include a plurality of holes with diameters of about 1 mm to about 3 mm. The distance between holes should be small and have regard to the diameters of the bumps on layer A3 so that the bumps do not penetrate the holes of layer A2.

According to an embodiment, cushion D may have the same structure as cushion A, including a tubinette envelope, and a protruded layer facing a cushioning layer which both include a plurality of holes. The two layers may be slightly curved toward the direction of the phalanges. According to an embodiment, these two layers may be inserted inside a tubinette envelope. The layers of E may have the same layers as cushion A as well. Cushions A, D, and E may be installed inside the internal walls 1001 of the brace 1000 by a fastening mechanism such as Velcro™ strips. The cushions may be removed and washed and reinstalled inside the brace as needed.

Cushions B and C may face the ankle and Achilles tendon. An additional layer B2 and C2 may be added to layer P as shown in FIG. 9 on top of the air bladders 702 and 703 as shown in FIG. 7.

Inside B1 there may be two layers B3 and B2. Layer B3 may be a multi-perforated membrane with domes facing the internal walls 1 of the brace 300. Layer B2 may be a flat, multi-perforated membrane. Between the two layers may be bumps allowing air to flow between them and reach the wearer's skin. The same structure may be found inside tubinette envelope C1, where the protruded layer C3 may have domes facing the internal walls 1 of the brace 300 and the multi-perforated layer C2 may be applied on top of layer C3. Since the cushions are not linked, cushions B and C may move forward towards the wearer's body part when inflated without pulling cushions A, D, and E from their original position. A securing mechanism such as strap Bt for securing the walking brace 1000 to the wearer is also shown. According to an embodiment, strap Bt may include a plurality of perforations which may enhance the aeration capabilities of the orthopedic support. According to an embodiment, the various detachable elements shown, such as cushions A, B, C, D and E may be covered from a porous fabric.

Figure 11:
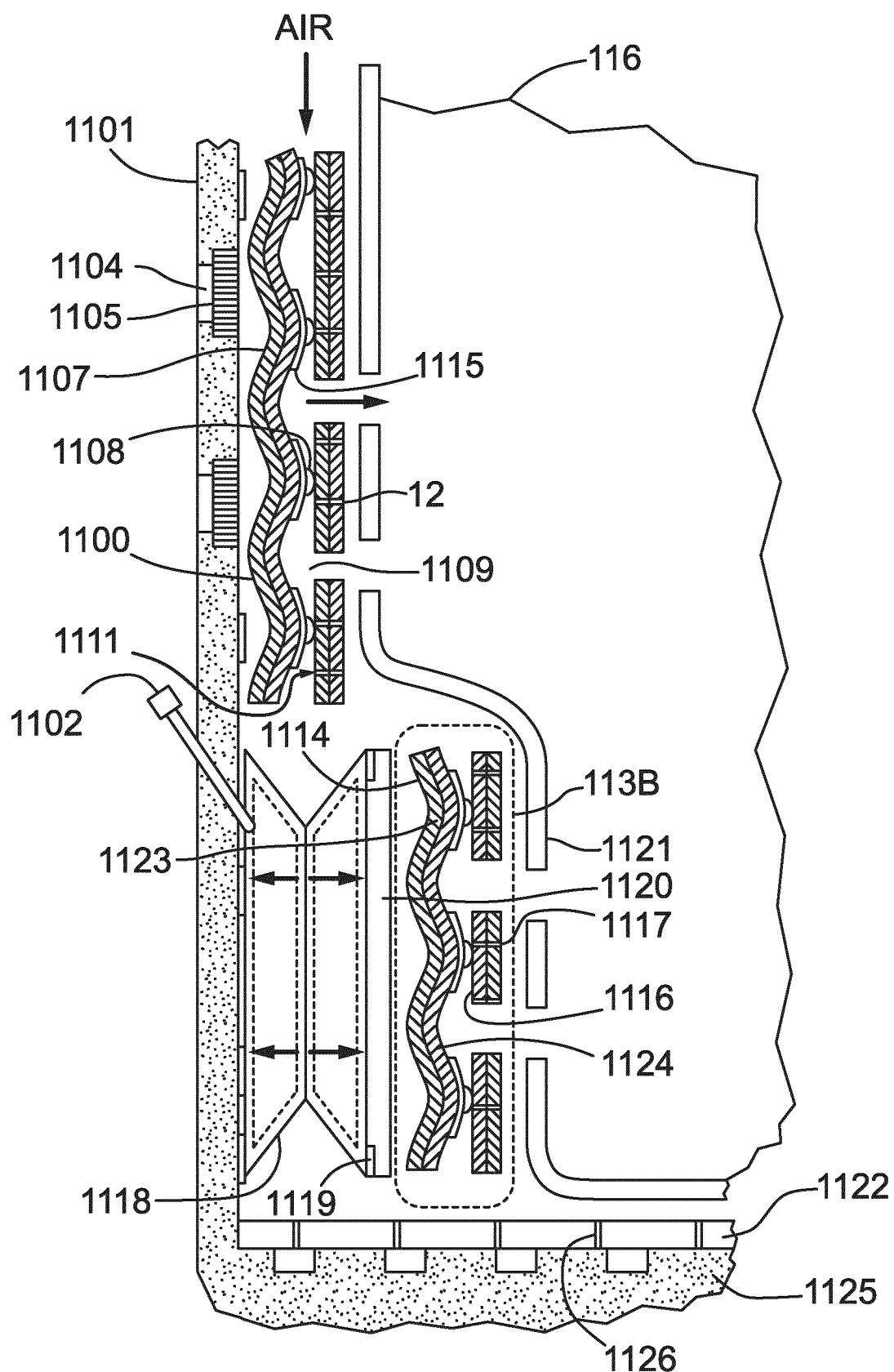
FIG. 11 is a cross-section of a walking brace shown when the air bladder is inflated according to an embodiment of the invention.

According to an embodiment as shown in FIG. 11, a cross-section of the walls 1101 of pneumatic walking brace is shown when the air bladder is inflated. The walls 1101 of the brace may be made of a polycarbon plastic material or similar material. Tubinette envelopes 113A (not shown, and may be optionally included) and 113B may be inside the walls of the brace and may be affixed by Velcro™ attachments. This may allow the wearer to detach tubinette envelopes 113A and 113B and wash the contents thereof while the inflatable "V" air bag 1118 may stay attached inside the brace. The tubinette envelopes 113A and 113B may contain two compressible layers. Layer 1107 may be a dual bumpy layer which may be made of EVA with spacer members such as protrusions 1115 and layer 1116 may be a multi-perforated membrane. Tubinette envelopes 113A and 113B may allow air to reach the wearer's skin 116 and may reduce the accumulation of heat as well as dissipate vapors before they condense and accumulate around the wearer's skin. The layer 1107 may include a first layer 1123 facing the internal walls of the brace and a second layer 1124 on top of the layer 1123, in which layer 1123 may be harder than layer 1124. When layer 1107 is compressed against the wearer, layer 1123 should be hard enough so as to not be flattened and maintain the shape of domes 1108 which define cavities therein. External air may circulate to and from and reside inside these cavities and therefore maintaining the shape of domes 1108 may help keep the wearer's skin fresh and comfortable.

Layer 1124 of dual layer 1107 may be softer and may provide more of a cushion to the wearer's skin. On top of layer 1107, there may be a soft and multi-perforated layer 1111 that may have a plurality of perforations, which according to an embodiment, may be small enough so as not to be visible to the eye.

According to an embodiment, the internal walls 1 of the brace may be equipped with a cushion enclosed by an envelope such as tubinette envelope 113A that may include a dual bumpy layer 1107 facing a multi-perforated layer 1111 and a cushion enclosed by an envelope such as tubinette envelope 1103B that may include a dual bumpy layer 1114 which may be made of EVA that may face a multi-perforated layer 1116. Air may enter from around the edge of the walking brace and may flow back and forth between layers 1107 and 1111 and between layers 1114 and 1116.

According to an embodiment, when inflated, air bag 1118 may look like a "V". When fully inflated, the lateral walls of the air bag 1118 may become vertically straight and uniformly filled with air thereby providing uniform compression to the anatomy of the wearer that faces the air bag 1118.

The air bag 1118 may also be equipped with a retractable plastified supportive surface 1120. Supportive surface 1120 may be situated on the lateral wall of the air bag 1118 via an adhesive and adjacent to its surface lies layer 1114 of dual hardness as well. Layer 1114 may have a first layer 1123 and its second layer 1124, wherein layer 1123 may have higher hardness than layer 1124.

According to an embodiment, sole 1122 may include perforations 1126.

Layer 1123 may be compressed by the air bag 1118 and should be hard enough so as not to flatten when compressed during use of the brace so that the advantages of having the domes 1118 would be lost. Layer 1123 may therefore act as a scaffold that may absorb the compressive or pushing force from the inflated air bag 1118. Layer 1116 may be compressed against the wearer as well when the air bag 1118 is inflated. In use, external air may travel from inside and around layers 1114 and 1116 towards and through perforations 1117 to the wearer's skin.

When the air bag 1118 is inflated, the walls of the air bag 1118 apply a force against the wearer through layers 1120, 1114 and 1116. This causes the retractable walls to expand and fulfill their function independently from layers 1117 and 1111. By having layers 1114 and 117 acting separately from each other, the air bag 1118 pushes layer 1114 against the wearer without pulling layer 1117 away from its supportive internal brace walls 1101. Therefore, two independent cushions enclosed by tubinette envelopes 113A and 113B may be provided which may be individually detached for washing or laundering by unfastening Velcro™ attachments 1113 and 1119.

Figure 12:
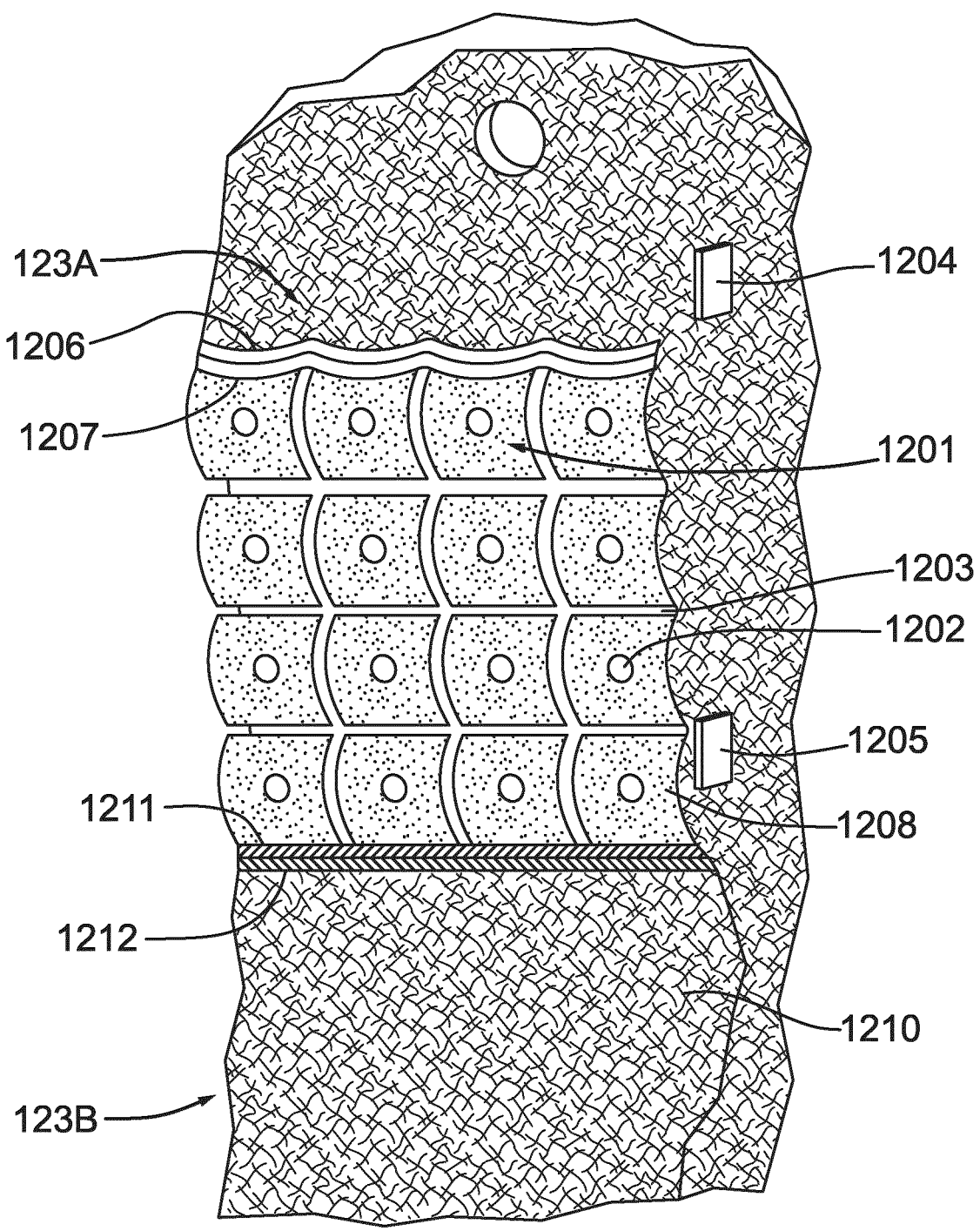
FIG. 12 is a fragmentary view of a portion of a walking brace with portions of both the exterior and intermediate layer removed according to an embodiment of the invention.

In FIG. 12, a fragmentary view of pneumatic walking brace is shown. Inside the brace's internal wall W, there may be a hollow tubular envelope or tubinette envelope attached. In FIG. 12, the wall W may be considered the first layer of the brace, and the tubinette envelope 123A may be considered the second layer. The opposite side of the tubinette 123B may be considered the seventh layer and may be situated closer to the limb's surface when the brace is worn by a wearer. Between tubinette envelope walls 123A and 123B may be four layers including a protruded dual membrane comprising a third layer 1206 and a fourth layer 1207 and a flat dual membrane comprising a fifth layer 1211 and a sixth layer 1212. Layers 1211 and 1212 may be made of EVA or silicone or gel or Plastazote™ or any equivalent material with hypoallergenic properties. Layers 1206 and 1207 may be made of two separated layers or alternatively of a single membrane. Layer 1206 may have a durometer of about 40 and layer 1207 may have a durometer of about 30. Having a layer 1206 with a higher durometer than layer 1207 may prevent the domes 1201 from collapsing when the dual membrane is under compression such as when the wearer is walking or when the leg is secured inside the brace by the Velcro™ straps or belts after the front panel is positioned over the lower leg. Therefore, layer 1206 may be considered to act as a scaffold because its high durometer may help to keep domes 1201 intact.

Layer 1207 may be of about durometer 30 which may offer a hardness strong enough so as not to collapse under pressure but that may still be soft enough to also provide a reasonable resting surface to the wearer. On top of layers 1206 and 1207 may be a layer 1211 of about durometer 30 which may face the spacer members such as protrusions 1202 of layer 1207. Since layer 1207 and layer 1211 have about the same durometer according to this embodiment, when these membranes are compressed against each other during use, the equal hardness may prevent the protrusions 1202 from penetrating the surface of membrane 1211.

Layer 1212 may have a durometer of about 20 which is softer than layer 1211. This lower durometer, depending on the present need of wearer, may be selected as a suitable hardness to keep the wearer's limb or other anatomy comfortable. Optionally, a further layer of a softer durometer such as about 1210 to about 1214 may be added on top of layer 1212 which may enhance comfort.

The aforementioned layers may be enveloped or enclosed by the tubinette's walls 123A and 123B and may be held together by adhesive, stiches, rivets or other similar attachment means. Adhesive or stitches or rivets may be applied on top of the protrusions 1202 around the perimeter of each aerated cushion, such as on top of the protrusions 1202 which may be located in the center of each cushion. Adhesive or stitches may keep the internal side of layer 1211 positioned against the protrusions 1202.

The tubinette's wall 123A may be attached to the wall of the brace with a Velcro™ attachment. The Velcro™ may be stitched to the cushion using a thread and stitch that may go from the Velcro™ attachment straight through the whole thickness of the cushion. The tubinette walls 123A and 123B therefore enclose a cushion that may be detached from the internal walls of the walking brace by pulling it away from the Velcro™ strips 1204 and 1205. The cushions may then be washed or disinfected and then placed back into the brace. The cushions may also be replaced with other cushions having smaller or larger areas and the layers or membranes therein may be substituted with other layers or membranes of different hardness or with materials such as antimicrobial agents.

FIGS. 13(*a*)-(*f*) shows a walking brace according to an embodiment during the assembly process. In FIG. 13(*a*), there is shown a walking brace A which may have a plurality of holes or openings 1302 over its walls 1301. Walls 1301 and base may be made of plastic as a one piece. The holes 1302 may have any shape or size suitable to allow for air flow while maintaining structural rigidity and being capable of providing sufficient protection and support.

In FIG. 13(*b*), the walking brace of FIG. 13(*a*) is now covered internally by a layer 1303 of hypoallergenic EVA which may include a plurality of holes. Air may enter through the holes 1302 shown in FIG. 13(*a*) and travel through the holes of the layer of EVA in FIG. 13(*b*) to the wearer's skin.

In FIG. 13(*c*), an inflatable air bladder 1304 may be affixed inside the brace A. A second air bladder (not shown) may be situated opposite to the air bladder shown.

In FIG. 13(*d*), the air bladder 1304 may be covered by a layer 1305 of EVA which may have a plurality of perforations. By this layer 8 being perforated, it may more readily adapt to the shape of the air bladder when the air bladder is inflated. Moreover, layer 8 may serve to shield the air bladder when the air bladder is forced towards and against the domes of layer M shown in FIG. 13(*e*). Without layer 8, the walls of the air bladder may cover the empty spaces of the domes in FIG. 13(*e*) when the air bladder is compressed against layer M. Accordingly, layer 8 may be considered to act as a scaffolding element.

In FIG. 13(*e*), layer M is shown which may be made of thermoformed EVA and includes a plurality of domes 1306 and a plurality of perforations.

Figure 13B:
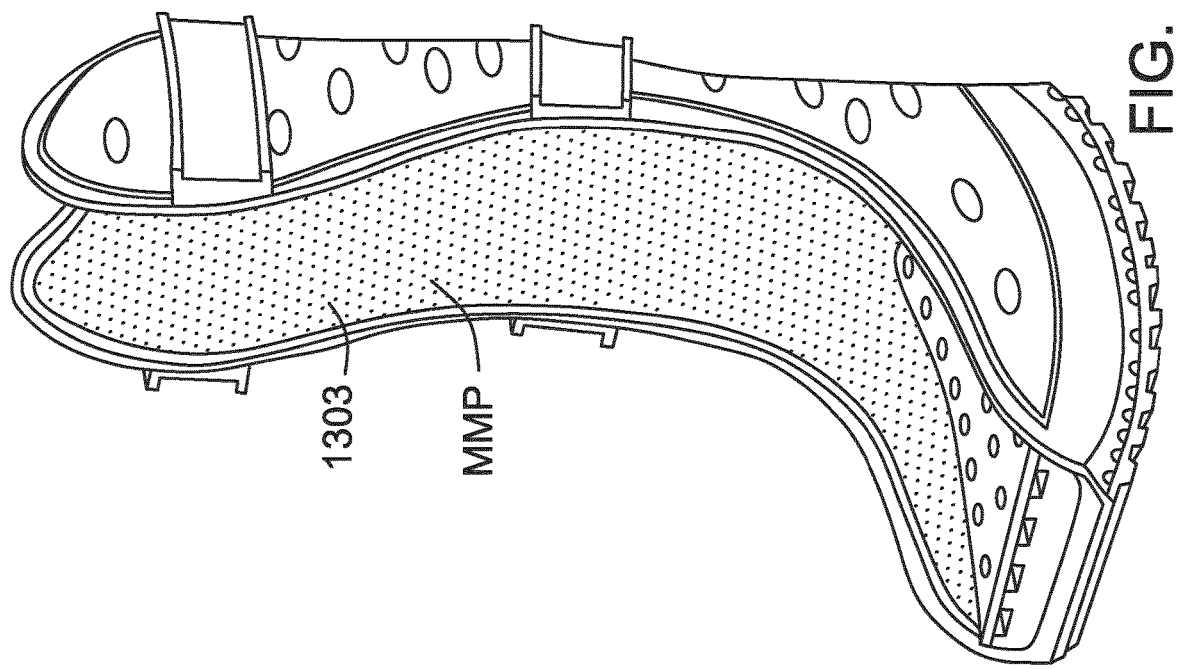
Figure 13A:
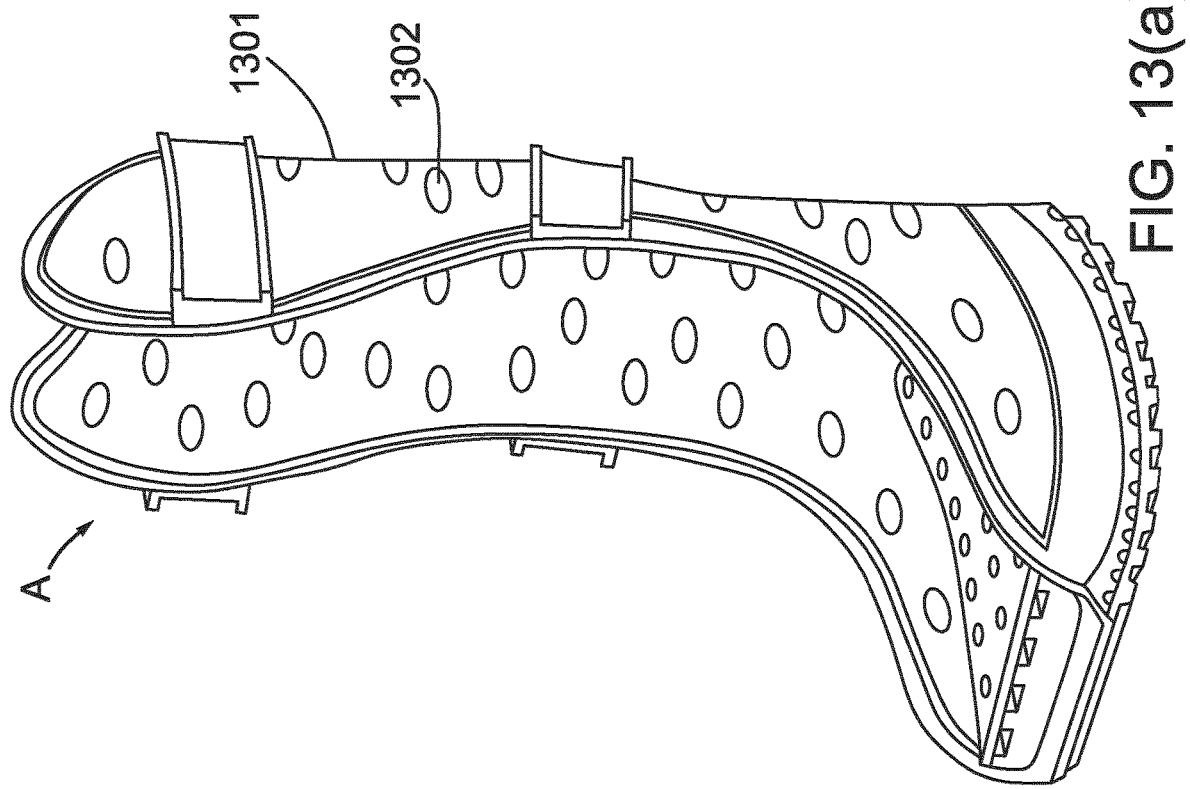
Figure 13D:
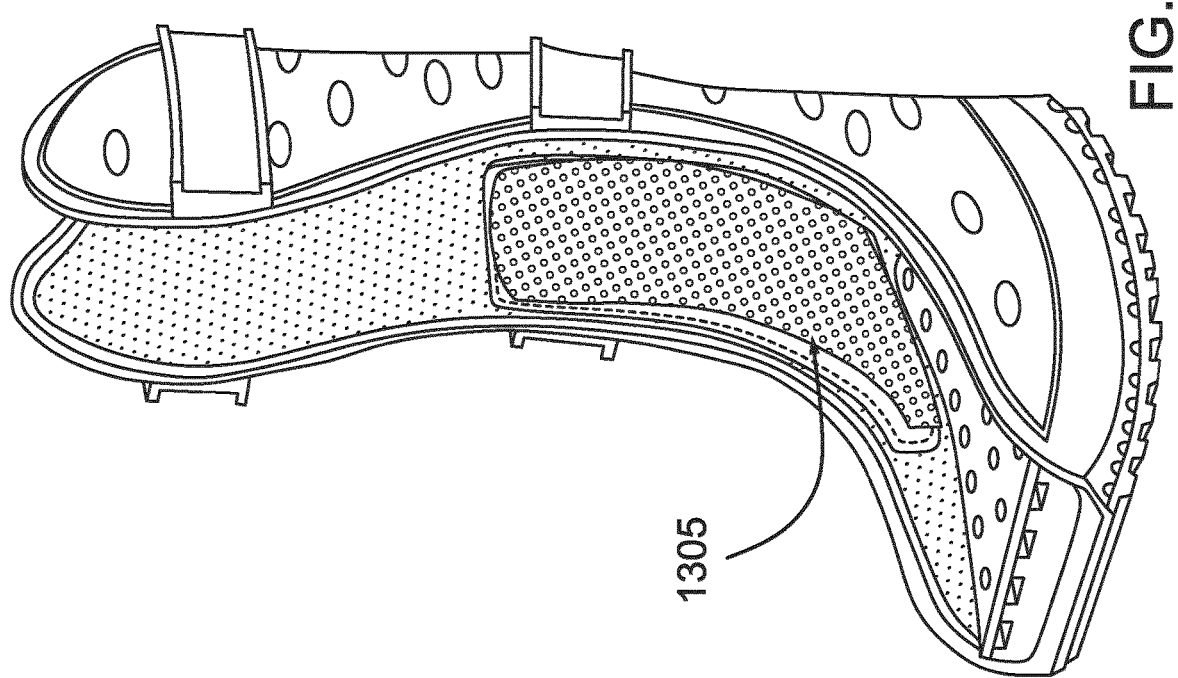
Figure 13C:
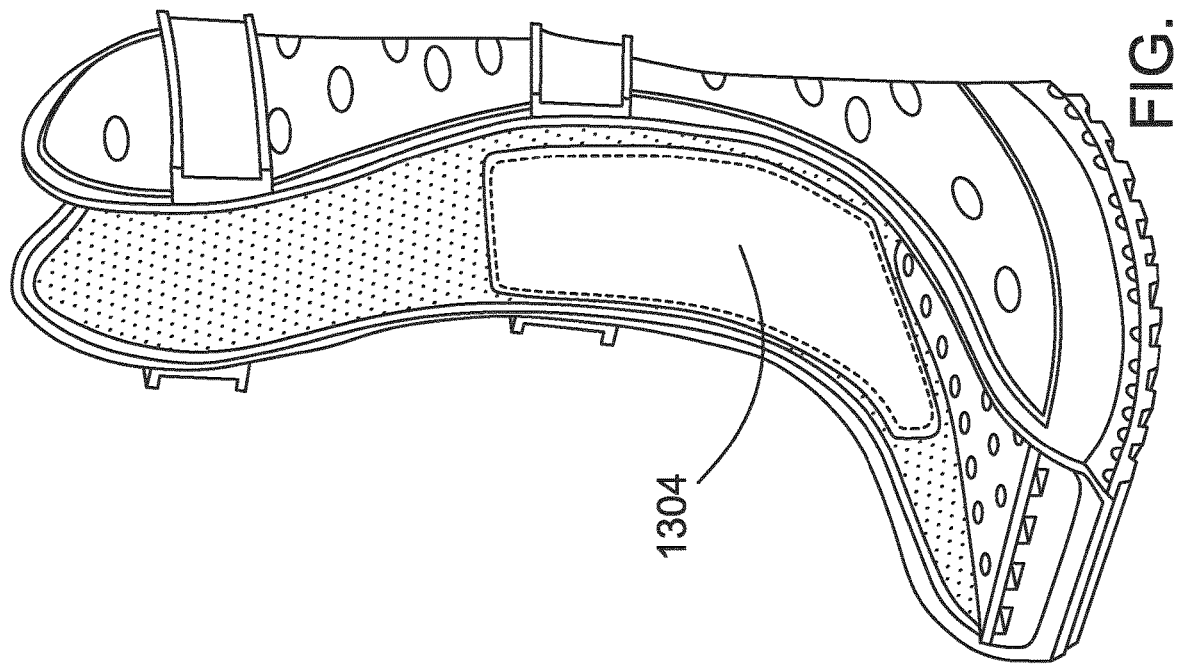

In FIG. 13(f), layer M may be covered by an additional EVA layer 1307, which may include a plurality of holes 1308 which may be about 2 mm or more apart and may have a diameter of about 1 mm according to an embodiment. 1310 and 1309 denote the respective edges of first layer and second layer respectively.

Figure 13H:
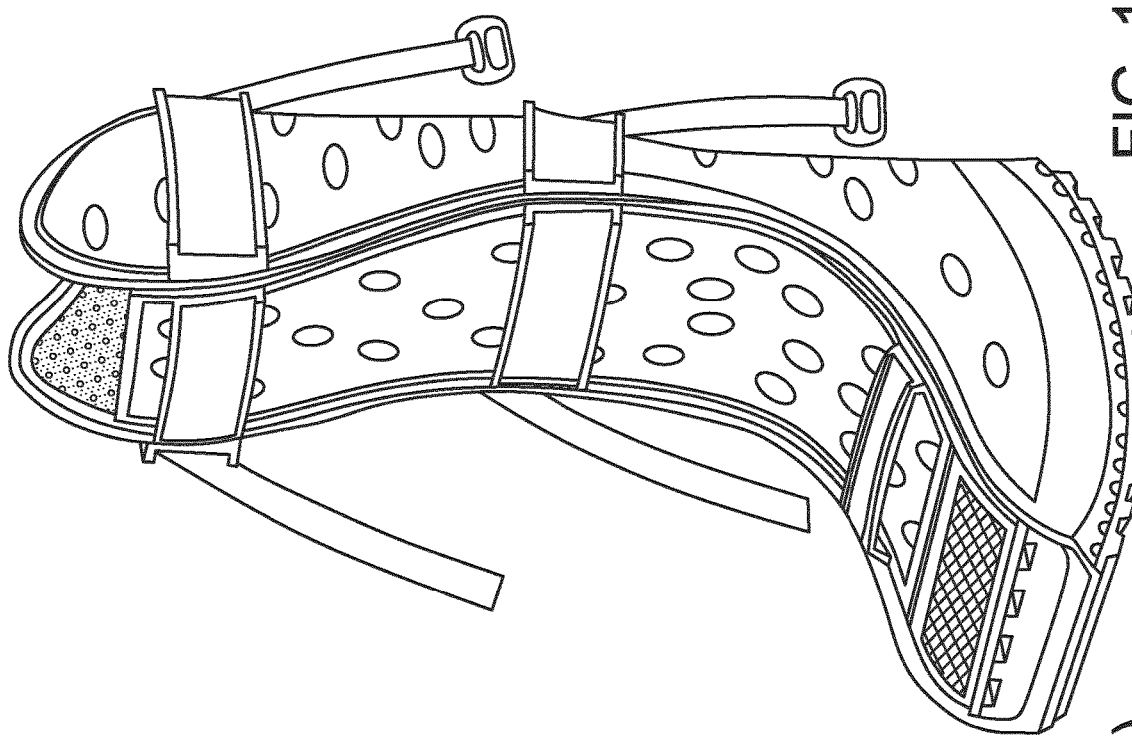
Figure 13G:
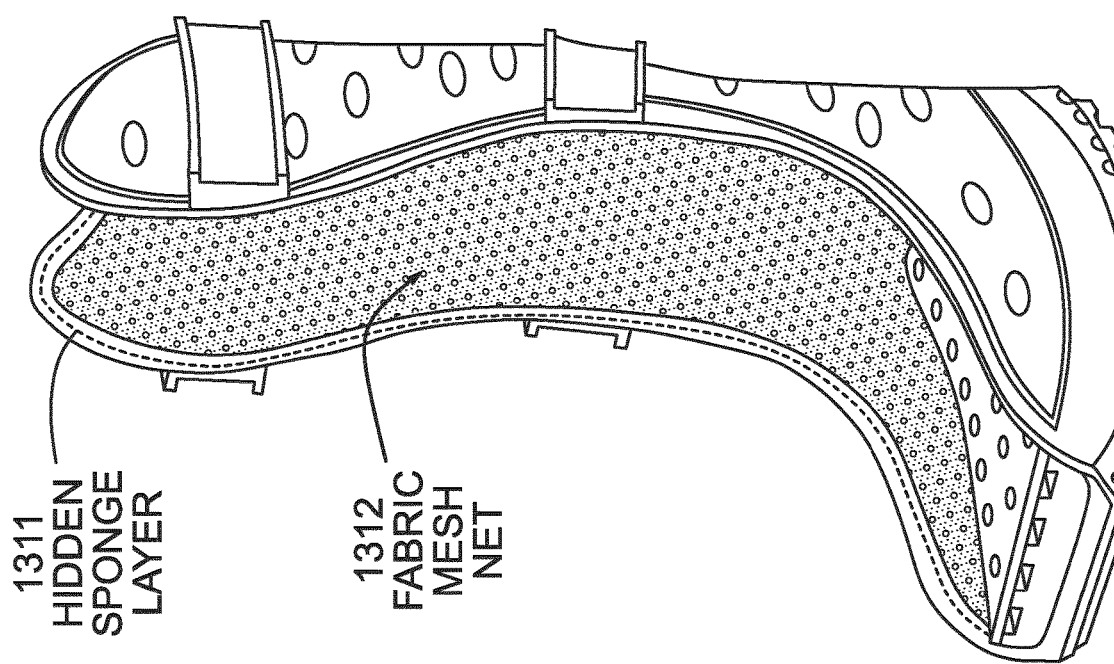

In FIG. 13(g), the walking brace is shown without the front cover. Fabric mesh net 1312 may been seen and there is a sponge layer 1311 hidden from view. In FIG. 13(h), the walking brace is shown with the front cover installed and the straps fastened.

Figure 14:
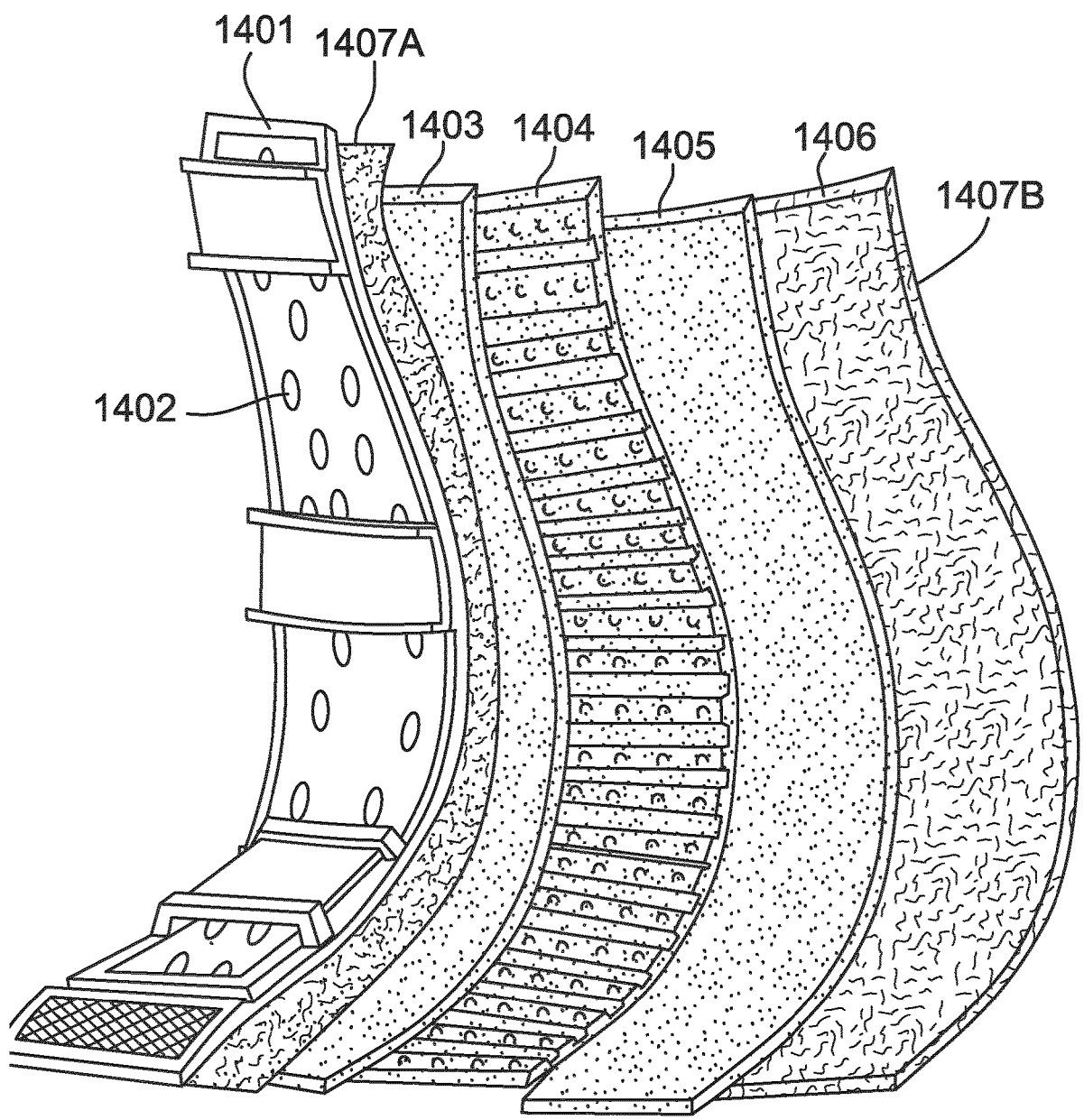
FIG. 14 is an exploded view of the successive layers of an orthopedic support according to an embodiment of the invention including a front panel.

FIG. 14 shows the successive layers of an orthopedic support according to an embodiment. The front panel 1401 of the walking brace may be made of a study protective material that may be pre-formed and contoured for a specific body part and may include holes 1402. Cover 1407A may be a brushed fabric with pores and may be laminated on top of layer 1403. Layer 1403 may be about 0.5 mm thick and made of EVA material and may include a plurality of perforations. Layer 1404 may be a 3 mm thick layer of EVA material and may be made according to the structure described in European Patent No. 2,107,899. Layer 1405 may be made according to the same construction as layer 1403. Layer 1406 may be a hypoallergenic foam of about 4 mm to about 6 mm thickness which may be made of open cells and may be light and aerating. Layer 1407B may be a mesh net fabric that may include a plurality of perforations and which may be laminated to the back of a foam layer 1406. Accordingly, layers 1403, 1404, 1405, and 1406 may be sandwiched between fabrics 1407A and 1407B and each may have holes to allow external air to pass there through. External air may also enter the empty spaces between the bumps present on layer 1404. Layers 1407A and 1407B may be stitched around the perimeters to prevent layers 1403 to 1405 from coming apart. The supportive pad comprising layers 1407A, 1403, 1404, 1405, 1406 and 1407B may be applied against the internal side of the front panel 1401 via Velcro™ or other suitable means. The combination of fabric and foam together may provide a soft, breathable, antimicrobial, hypoallergenic supporting pad that may be removed from inside of the walking brace to be washed or replaced by a new one with the same or different characteristics.

Figure 15:
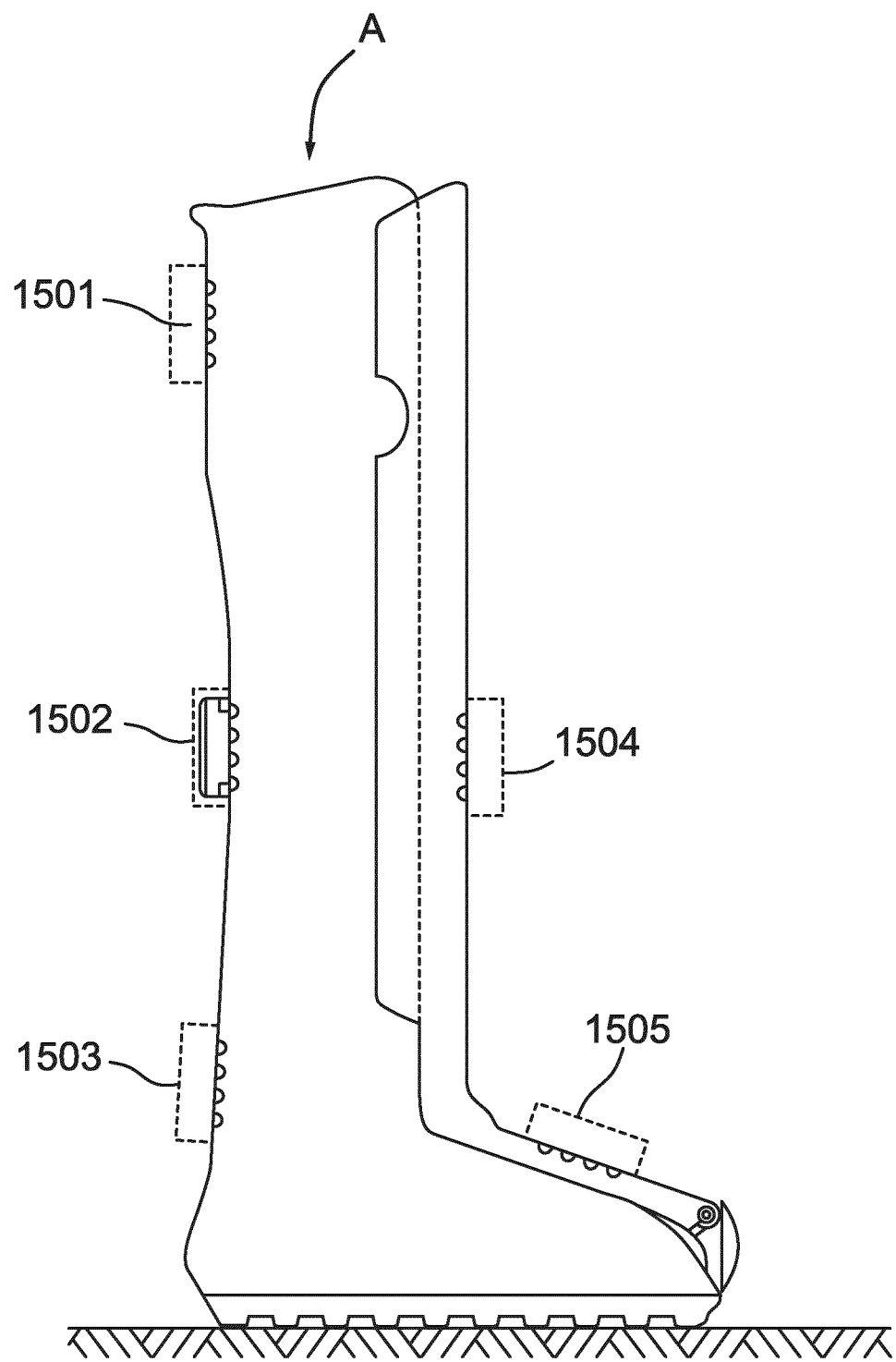
FIG. 15 is a side view of a walking brace according to an embodiment of the invention.

FIG. 15 shows a walking brace A according to an embodiment of the invention. Front panel or shield S may have a window FW which may include a plasticized net for aeration of the phalanges and the toes. FW may be positioned by means of a hinge H. This moveable window may provide more comfort to the wearer as the hinge H and window FW may be removable. The window may be internally concave (like a large spoon) and thereby may allow more space and protection for the toes.

According to an embodiment, a centrifugal blower CB may be positioned at positions 1501, 1502, 1503, 1504, or on the external sides of the brace A and may send external air to the wearer's skin or other anatomy through holes HO situated in the walls of the brace A. If it is positioned at locations 1501, 1502, or 1504 then the wearer should avoid long trousers as the centrifugal blower could attract or vacuum the trouser fabric. The centrifugal blower may be remotely operated either wirelessly through the use of a wireless transceiver or by wired connection and may be powered by silver oxide or lithium batteries.

According to an embodiment of the walking brace, the following exemplary materials may be used: polypropylene for the shell, high density polyethylene for the front panel, nylon for the straps, polyurethane with polyester fabric for the lined air cells (both anterior and posterior), thermoplastic polyurethane for the inflation pumps, nylon, polyurethane and polyester for the liner for the outer foam and inner mesh, polyester for the binding, EVA and rubber for the outer sole and insole, nylon for the selector dial and acrylic or cotton for the sock. The shell should be thick enough to provide the required rigidity so that the walls of each shell section do not bend to any significant extent. In other words, each shell section may be made sufficiently rigid so that the overall exterior shell may serve its function as a brace that will support the enclosed body part and not permit undesirable movement thereof.

FIG. 16 is a partially exploded side view of a walking brace according to an embodiment of the invention. The brace A may be long and come up to the wearer's knee or may be short and immobilize the ankle's movement. The brace A may have a main body 1601, a front cover 1602 (shown removed), holes 1603, a removable toe cover 1604 and a rubber base 1606. The removable toe cover 1604 may help shield the toes from injury. The removable toe cover may be perforated so as to allow external air to access the wearer's foot. The front cover 1602 may be made of two or more pieces that may be mechanically attached. The edges of the front cover 1602 may face the edges of the main body 1601 or may be adhered underneath the edges. The edges of the front cover 1602 may also cover the edges of the main body 1601 when installed on top of the wearer's leg. The edges of the main body 1601 may overlap the contour of the toe cover 1604 as well.

According to the embodiment shown in FIG. 16, the holes 1603 may have diameters from about 2 mm to about 10 mm wide and may be made of any shape suitable for allowing air to flow through for aeration. It should be appreciated that the more holes, or the larger the holes are, on the brace, the weaker the brace becomes, and the walls may need to become thicker in order to be sufficiently strong and protective.

Figure 16A:
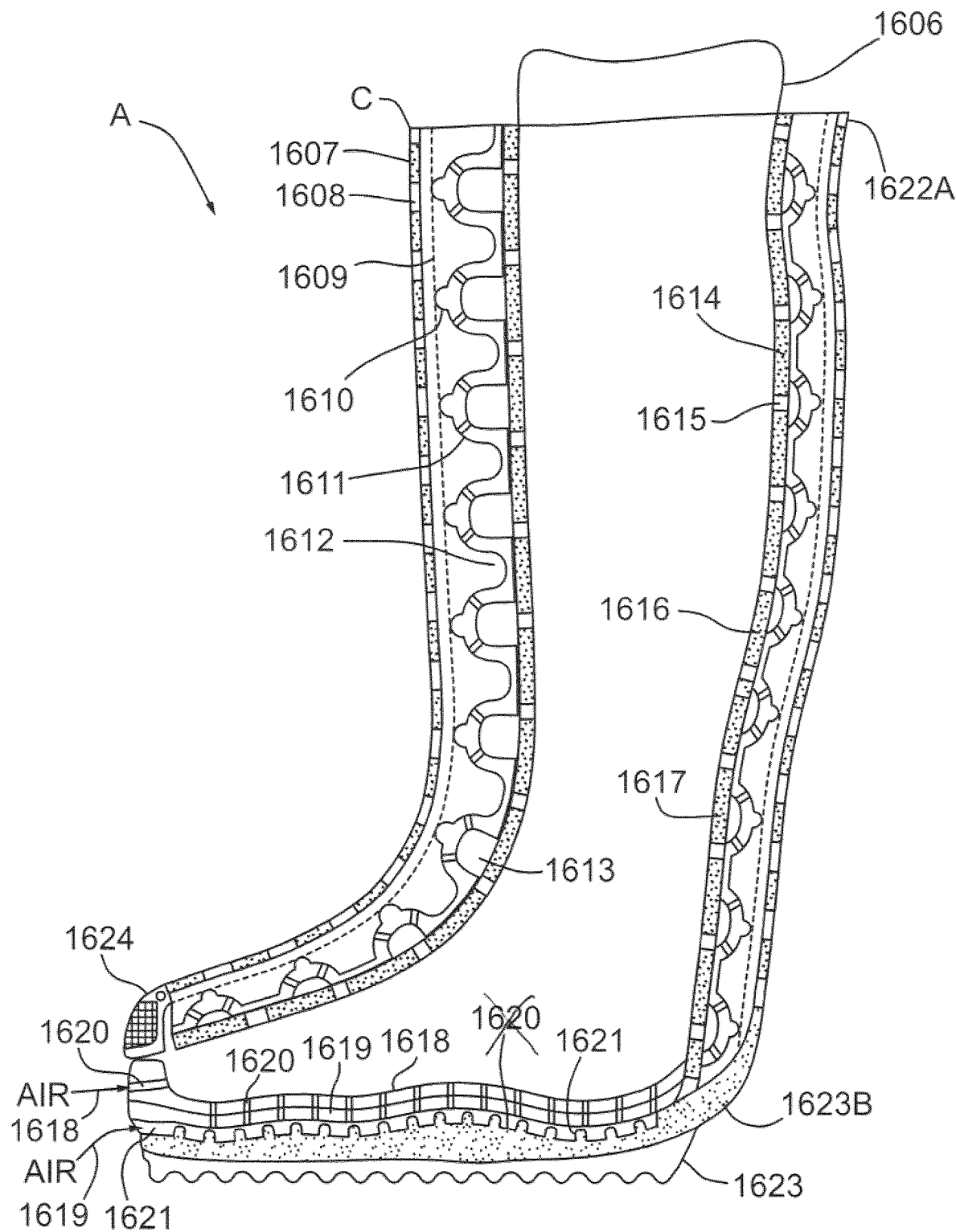
FIG. 16(a) is a cross-sectional view of a walking brace according to the embodiment shown in FIG. 16.

According to the embodiment shown in FIG. 16(a), the front cover C is shown installed on the brace A. The wearer's leg 1 is shown within the brace A. The walls 1607, 1622A, 1623B of the brace A may include a plurality of holes 1608. Inside the walls of the front cover C and walls 1607 and 1622A there may be a layer of EVA mesh net 4 which may help prevent protrusions 1610 from coming out of the holes 1608. The protrusions 1610 may allow the cavities 1613 to be further away from the internal walls of the brace. This may provide more empty space 1612 within the brace A and therefore better air circulation to the wearer's skin. The protrusions 1610 and the domes around cavities 1613 may be made of a thermoformable, hypoallergenic EVA material.

External air may penetrate the brace A through the holes 1608 and then flow through the holes 1611 and the domes surrounding cavities 1613 and then through the holes 1615 of a foam layer 1614 and then to the wearer's skin. The foam layer 1614 may be a supporting pad that may be laminated internally by a mesh net fabric 1616 by heat flame. The foam layer may be laminated externally as well by a porous fabric such as brushed textile 1617.

The brace A may provide for aeration through the bottom of the brace A as well. External air 1618 and 1619 may enter the brace A through channels 1620 and 1621. At the bottom of the brace there may be a plastic wall 1623B, which may be thicker than lateral wall 1622A. Wall 1623B may include protrusions or bumps 1621. Bumps 1621 may be made of the same material as wall 1623B, which may add more strength to the brace A and may make it less prone to damage during use. External air may enter in between the bumps 1621 and may flow upwards towards the bottom fasci of the wearer's foot via the holes 1620 in the EVA sole 1618. According to an embodiment, the sole 1618 may be made of two layers. A top layer is made of a hardness of about 30 to about 40 durometers, which be soft enough to provide a comfortable supporting base. Underneath the top layer is a layer 14 which may be made of EVA and may have a hardness of 60 to 80 durometers. Layer 14 may protect the base of the wearer's foot from sinking inside the empty spaces at the bottom of the brace A.

According to an embodiment, brace A may have a frontal shield 1624 and may have a mesh net (not shown). The mesh net may allow external air to enter the walls of the frontal shield 1624 and may prevent external matter such as pebbles or stones from penetrating the brace A and causing damage to the wearer's foot. Similarly, in front of the entrances to the channels 1620 and 1621, there may be a filter (not shown), these filters may prevent external matter such as pebbles or small stones from entering the brace A.

FIG. 17 is an exploded view of laminated foam which may be employed in an orthopedic support according to an embodiment of the invention. There is shown a sheet of hypoallergenic foam 1704 which may be about 6 mm to about 8 mm thick according to an embodiment. On its surface there may be holes or perforations of about 3 mm to about 5 mm in diameter according to an embodiment. Other thickness and diameters of holes may be used depending on the particular application. On top of this foam 1704 may be a brushed fabric 1702 that may be laminated thereon using flame technology or similar means. On the opposite side of the foam 1704 there may be a second piece of fabric called mesh net 1703. It may be laminated towards the foam 1704 by flame technology or similar means.

Figure 18A:
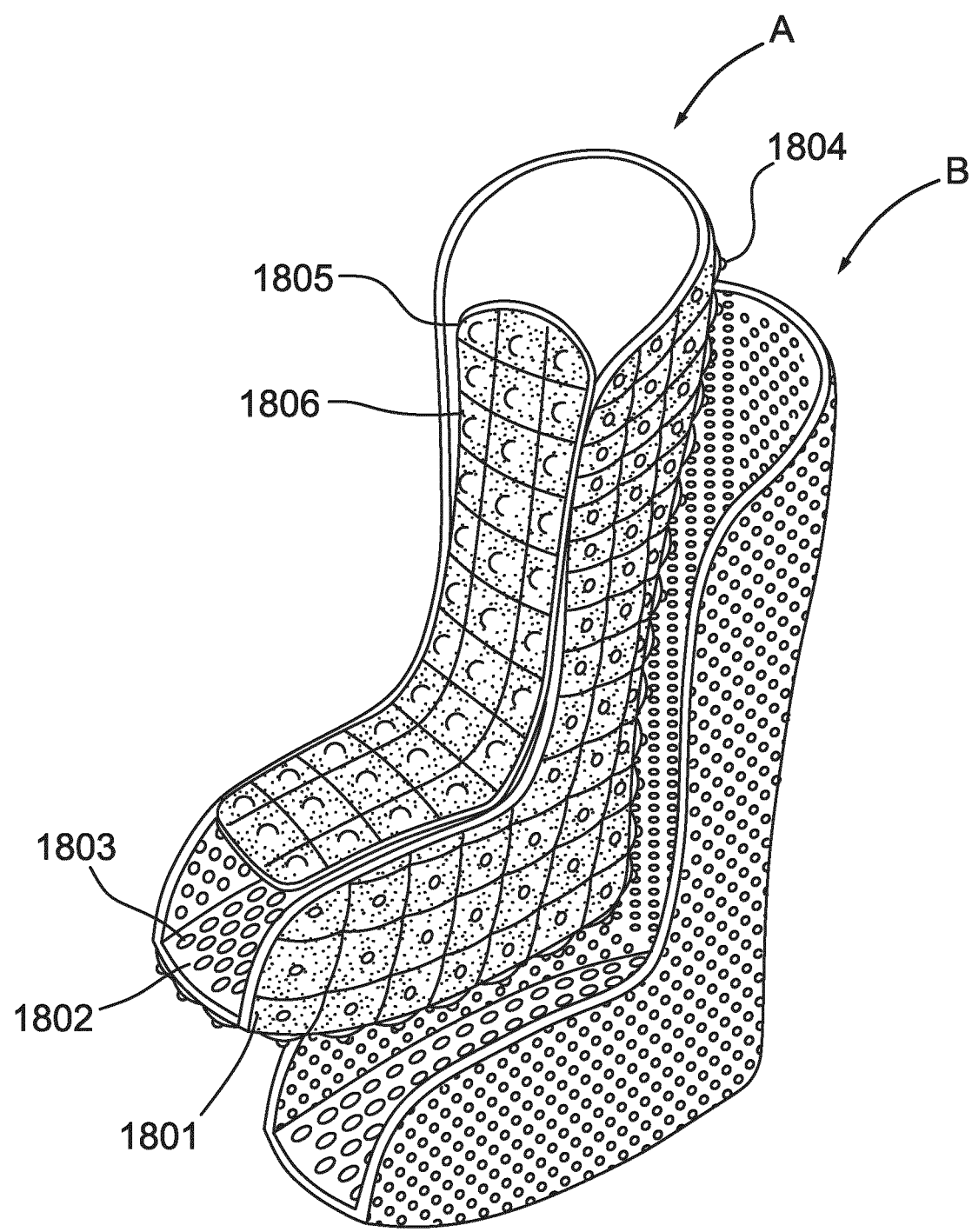
FIG. 18(a) is an exploded view of a walking brace including a double boot according to an embodiment of the invention and FIG. 18(b) is an exploded view of a walking brace according to an embodiment of the invention including a double boot and front panels.
Figure 18B:
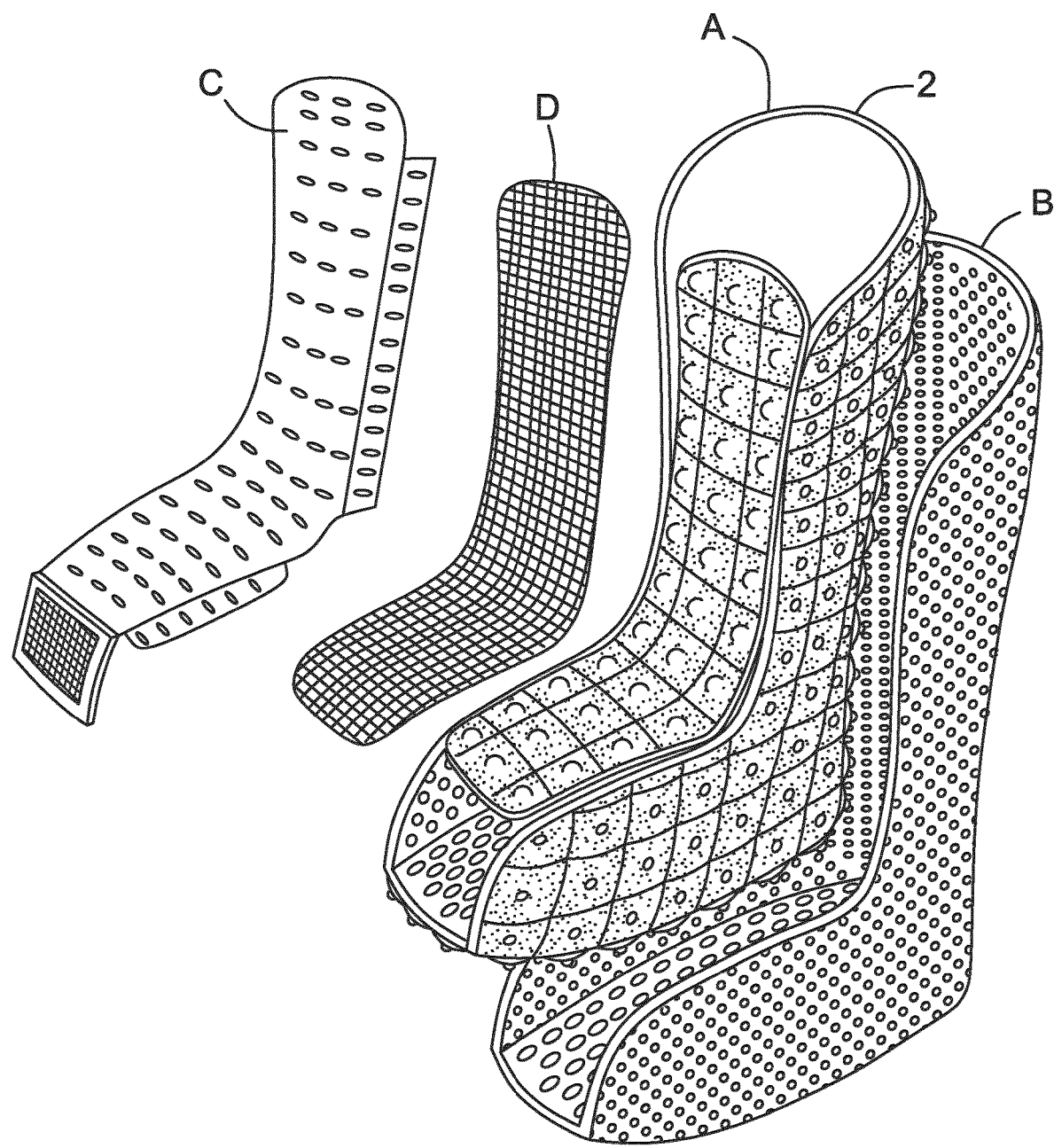

FIG. 18(*a*) is an exploded view of a walking brace according to an embodiment of the invention. FIG. 18(*a*) illustrates how boot A may be inserted inside boot B. As shown boot B may be larger than boot A such that the external dimensions of boot A may be approximately equal to the internal dimensions of boot B. Alternatively, a soft pad of foam that may be laminated with breathable fabrics on both of its sides may be inserted inside the walls of boot A. The laminated foam may have a plurality of perforations 1801 which may be made by a steel rule die or similar means. The laminated foam may add more soft support to the wearer, as well as more aeration and comfort. The soles 1802 which may also have hole 1803 may have adequate hardness so as to prevent damage to the protrusions 1804 that lie externally under the wearer's foot. The double boot may also be used around a limb that may be enclosed by an immobilizing fiberglass cast. In this case, the laminated foam may not be needed as cotton may be applied around the wounded limb. Ridges 1805 and holes 1806 may be include on the front panel as is also shown.

FIG. 18(*b*) is an exploded view of a walking brace according to an embodiment of the invention. There may be a shell of boots A and B of medium softness with a plurality of perforations as shown in FIG. 18(*a*). Front panel C may be made of plastic. Panel D and the front panel of boot A may be pre-fastened together. Panels C and D and the front panel of boot A may be installed, one on top of the other, in the same order as in this figure and may be anchored together by Velcro™ straps. Alternatively, front panels C and D and the front panel of boot A may be assembled as a single piece. Panels C and D, may be installed after the wearer places his or her lower leg inside of boot A which may be inside of boot B. The brace may then be closed via nylon straps, such as Velcro™ straps.

According to a further embodiment, elements of the brace shown in FIG. 18(*b*) may be used under a fiberglass cast so as to provide a non-walking cast. The wearer's lower leg may be placed inside boot A and then covered by a front panel and then panel B may be placed on top of the front panel of boot A. According to an embodiment, the front panel of boot A and panel D may be pre-fastened together such as with plastic fasteners or by stitches or by adhesives or other suitable fastening means. When this embodiment is used as a non-walking cast, softer cushioning material may be used in the sole whereas harder materials may be used in a walking cast. The harder base may prevent the external bumps of the soles from collapsing when the weight of the wearer is exerted on the device. The front shield may be anchored to the posterior of the cast and the device may be molded such that the foot may be inclined at 90 degrees or more. Such inclination may be desirable for wearer's that have had Achilles tendon surgery.

FIG. 19(*a*) is an exploded view of successive layers of an orthopedic support according to an embodiment of the invention. The brace shown may be for an upper limb and may be used to immobilize and protect any part of an arm. R denotes the location of the wrist while E denotes the location of the elbow. The brace may be include an outer layer A" of hard plastic in the form of an external L-shaped front cover which may include a plurality of openings 1908. Strap 2A" may be included for securing the orthopedic support to the wearer.

Layer A' may have a hole H' which may let the wearer's thumb through when the brace is installed. Outer layer A' may cover the front cover A" and A' and A" may be closed by nylon straps. Inside the brace consisting of A' and A", there may be another pad made of EVA including a first layer front cover B'. This cover B' has a hole H" which may allow the thumb to pass through when the brace is installed. It may also have a plurality of spacer members such as protrusions 1903 and a plurality of holes 1902. Between the protrusions 1903, there may be grooves 1904 which may allow the support to be more flexible.

Shell B" may be made of EVA and may have a durometer of about 15 to about 25. Shell B" may also have protrusions 1906 as well as a plurality of holes 1905. In FIG. 19(*a*), R denotes the wrist area, while E denotes the elbow area of the brace. External air may travel between the protrusions 1906 and may reach the wearer's skin through the holes 1905. Grooves 1907 may also be included. The brace may be as long as shown, but alternatively may be made to cover only the segments of the wrist or carpus to the metacarpus, or alternatively may be made to cover only the forearm such as the radius and ulna, the humerus with the radius and ulna at 90 degrees or at a different angle as needed.

FIG. 19(*b*) shows the brace of FIG. 19(*a*) fully assembled. According to an embodiment, it may cover the wearer's whole arm from the hand to the shoulder. According to further embodiments, the brace may be made in other sizes and configurations that only partially cover the wearer's arm. For instance, the brace may immobilize the hand and wrist up to point 01 or may be manufactured to immobilize the forearm from point 01 to point 02, if desired. According to further embodiments, it may be made to immobilize the arm only from point 02 to point 03.

According to an embodiment, the brace may be made of plastic and have openings or holes 3. Internally, it may have a layer 10 of EVA material made in the manner previously described. The layer 10 may have a plurality of protrusions 12 and between the protrusions there may be channels or grooves 11. The brace may allow the thumb to be exposed as shown through thumb opening 6. The shield 1 may cover the shell 2 thus immobilizing the wrist 7 and the elbow 8 of the wearer. In use, the straps 4 and the buckles 5 may tightly close the shield 1 towards the shell 2. The brace may then be opened by withdrawing the shield 1 up and away from the wearer's torso.

Figure 19A:
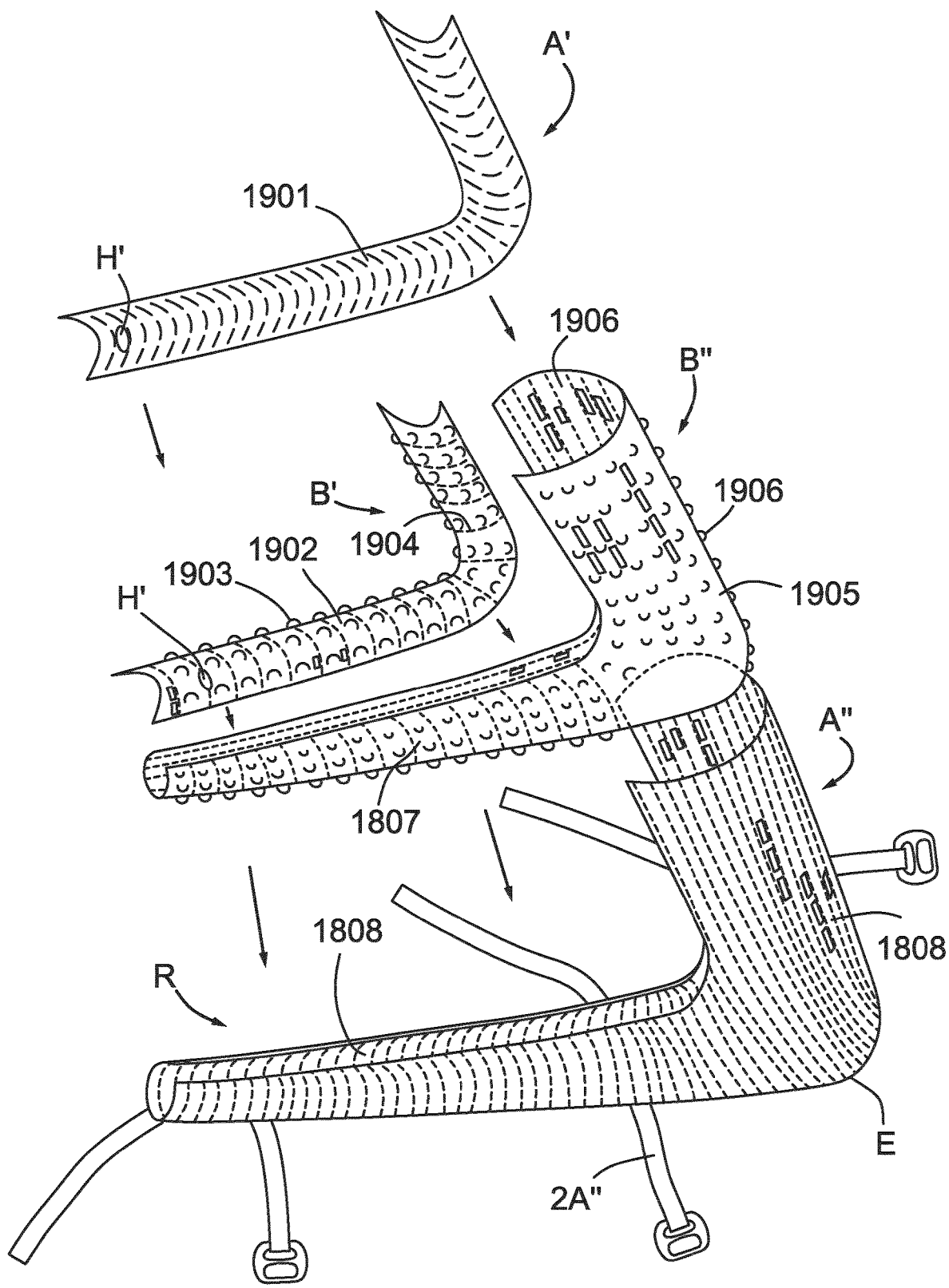
FIG. 19(a) is an exploded view of layers of an orthopedic support for an upper limb according to an embodiment of the invention.
Figure 19B:
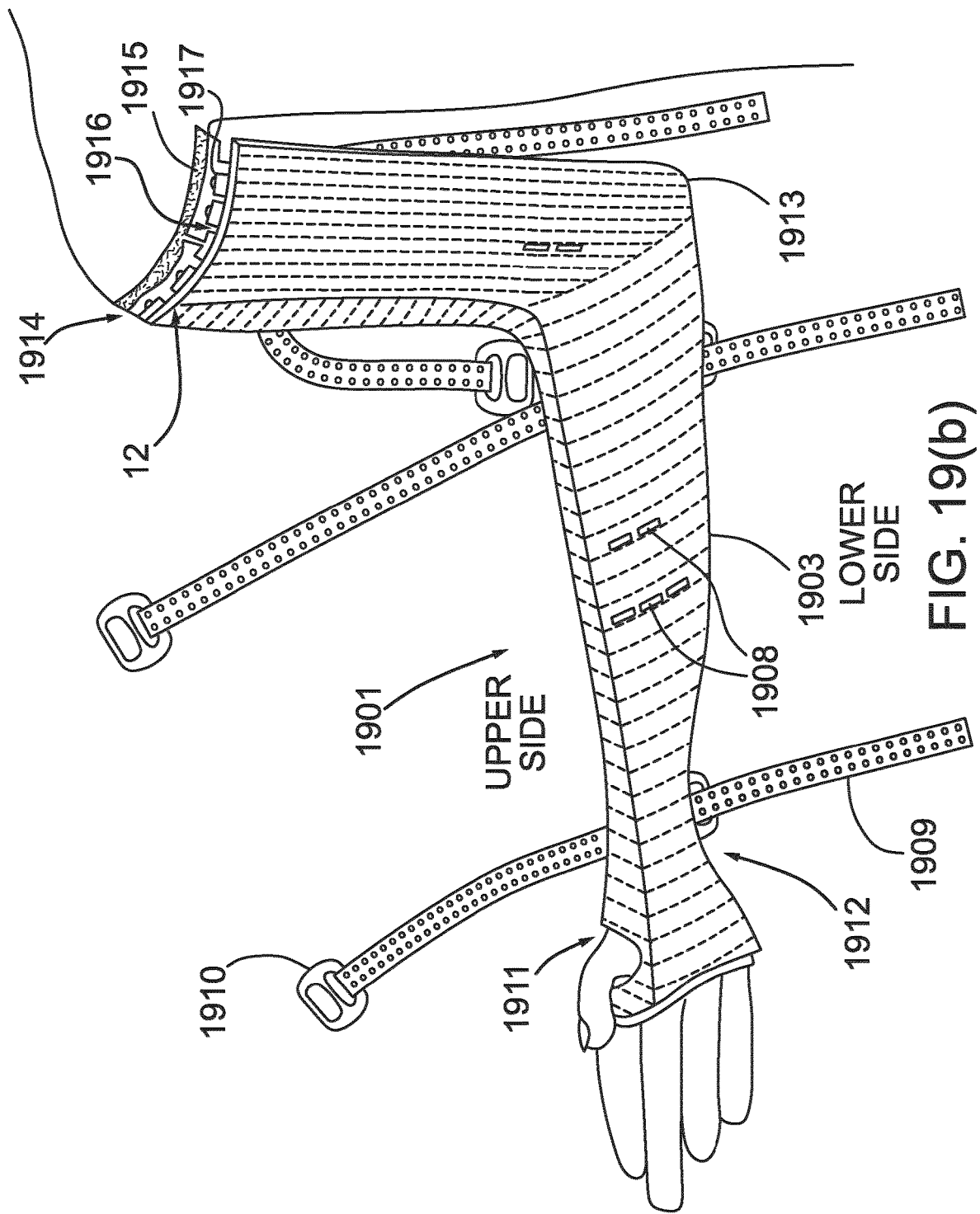
FIG. 19(b) is a side view of the fully assembled orthopedic support for an upper limb shown in FIG. 19(a)

According to a further embodiment, the brace of FIG. 19(b) may be used without the shield 1901 or the shell 1903 which may include openings 1908 over an immobilizing cast such as a fiberglass cast. In this embodiment, the layer 1915 made of the perforated EVA that may include protrusions 1917 and grooves 1916 and may allow for circulation of air to the wearer's limb. Optionally, the wearer's skin may also be covered with cotton 1914 or with a tubular stockinette or wound dressing pads. Thumb opening 1911 may be included and the straps 1909 may surround the wrist 1912 and may include buckles 1910.

Figure 19C:
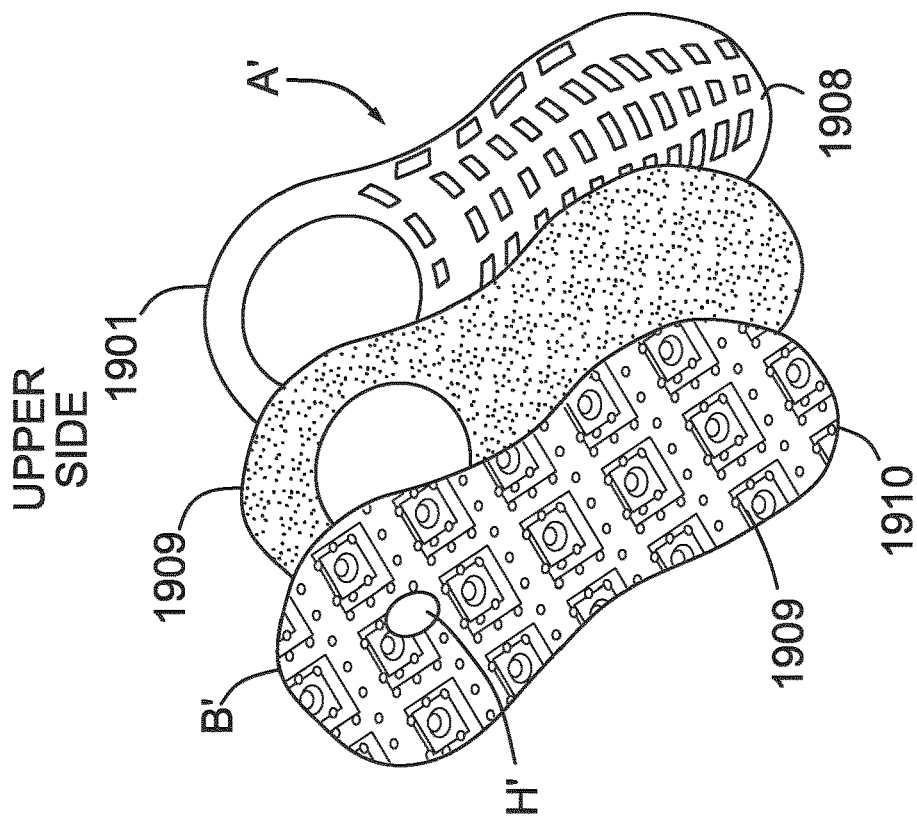
FIG. 19(c) is an exploded view of the layers of an orthopedic support according to an embodiment of the invention.
Figure 19C:
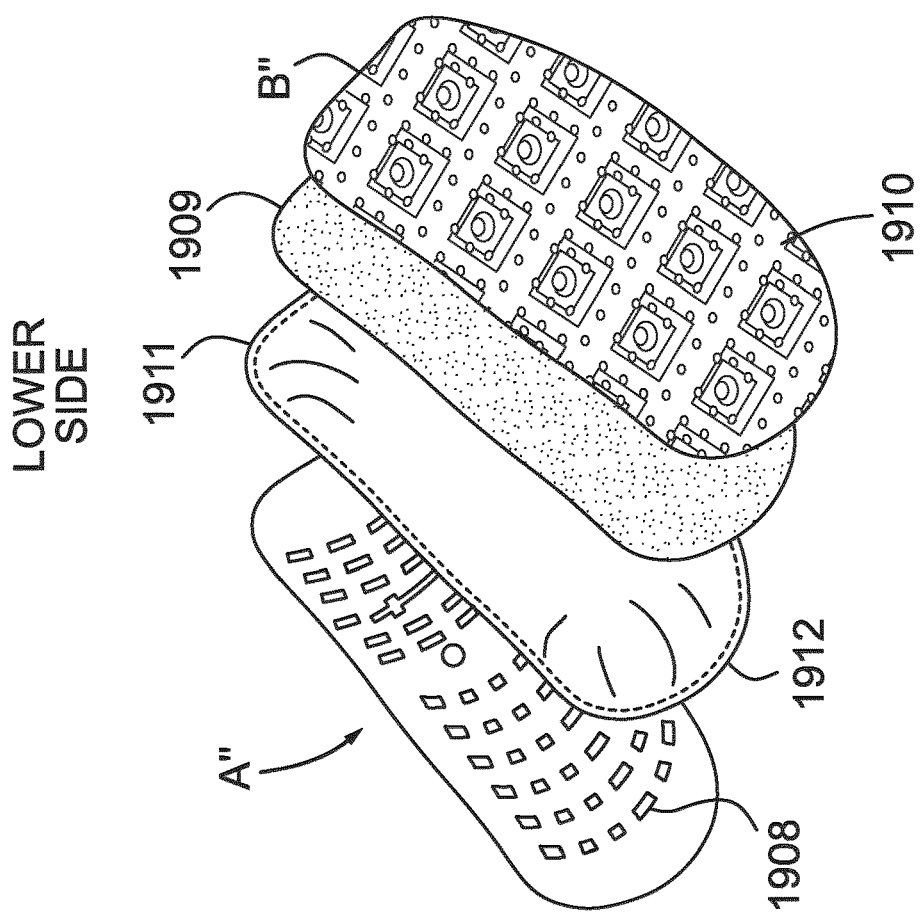

FIG. 19(c) is an exploded view of successive layers of the orthopedic support of FIGS. 19(a) and 19(b) according to an embodiment of the invention. In this figure, the brace is configured to partially cover a hand and a forearm. The left side of the brace is shown by parts A", 1911, 1909 of LOWER SIDE, and B", whereas the right side of the brace as shown by parts 1901, 1909 of UPPER SIDE, and B'. These parts may be assembled and secured around the wearer's limb via nylon strips such as those made of Velcro™. Thumb hole 1909 may allow the thumb to pass through. Optionally, air bladder 1911 may be included which may have plastic walls may be situated around the perimeter 1912. An air cannula and hole for the insertion of air cannula may also be provided as shown.

The external walls A" and A' may have holes 1908 to allow for aeration of the wearer's skin and may also make the orthopedic support lighter. Optional layers 1909 and may be made of EVA, or polyurethane, or any equivalent thermoformable plastic or injectable plastic. The layers 1909 may have holes and may protect the optional air bladder 1911 from being partially penetrated by the bumps of the domes 1910. Layers 1909 may act as a scaffolding support. Layers B" and B' may be made of EVA, or Styrofoam™ or any equivalent thermoformable or injectable material. The layers B" and B' may have a plurality of holes and cavities formed underneath domes 1910 that may face the wearer's skin. The cavities may allow air to flow there through and may increase the aeration and circulation of air in the brace as the layers 1909 are not in flat contact due to the shape of domes.

Figure 20:
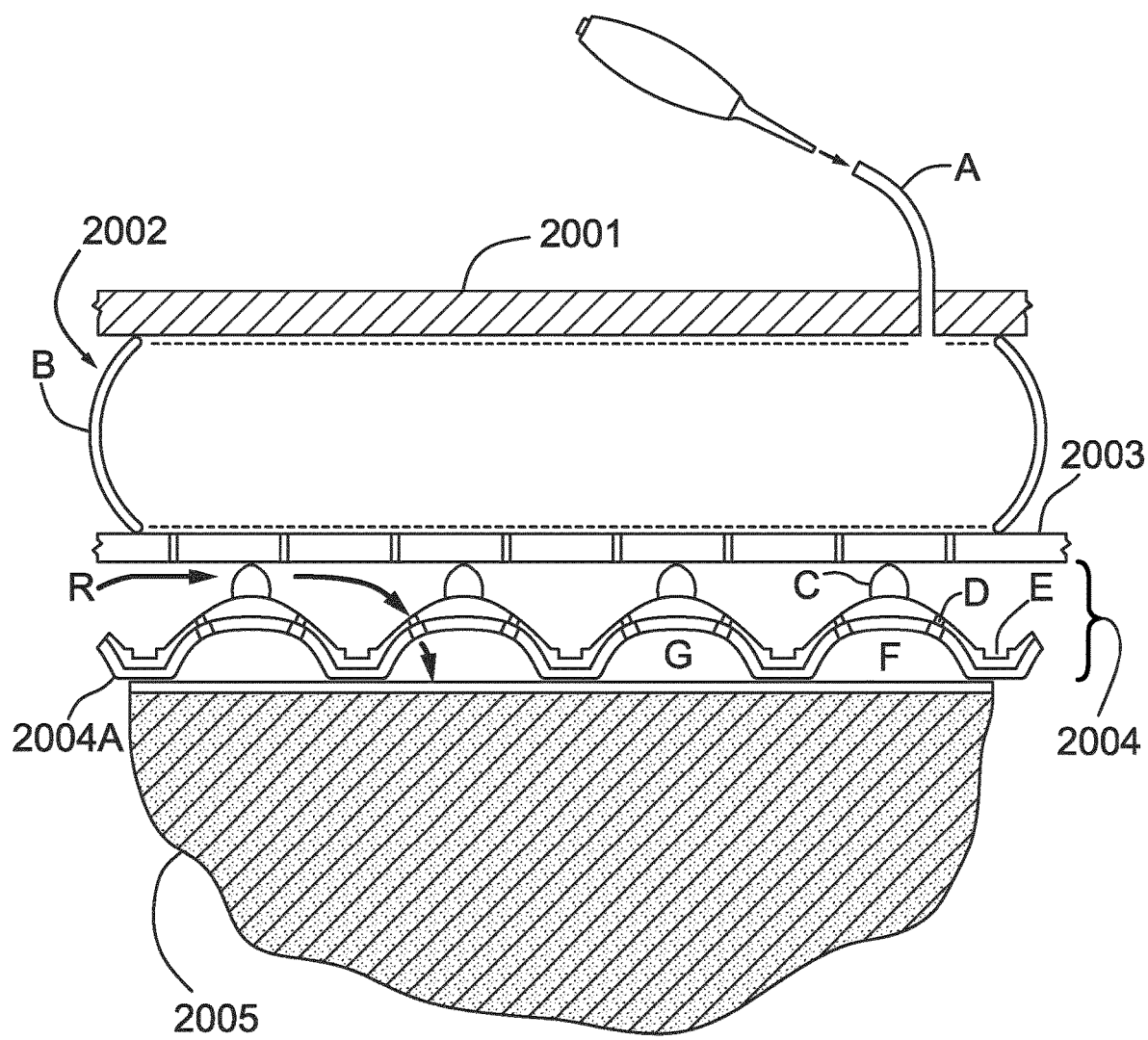
FIG. 20 is a cross-sectional view of a brace including an air bladder according to an embodiment of the invention.

FIG. 20 shows an embodiment of the invention which includes an inflatable air bladder 2002 which may provide compression against the wearer's limb. The embodiment may include a layer as described herein made of a plastic, or EVA, or polyurethane or Styrofoam™ inside the brace to allow for external air to enter the brace and flow to and from the wearer's skin. Prior art braces which include air bladders often have them in direct contact with the wearer's skin which provides compression but does not allow adequate aeration and therefore the wearer's skin may become hot. According to this embodiment, the brace may have plastic walls 2001 which may surround the limbs of a human or animal. Air bladder 2002 may be situated behind the walls 2001. When air is introduced inside the air bladder 2002 via the air duct A, the walls B of the air bladder 2002 may be compressed against the surface of the wearer's skin 2005. Between walls B and the surface layer of skin 5, there may be a scaffolding mesh net layer 2003. Layer 2003 may lie on top of protrusions C of layer 2004 which may be made of EVA. Layer 2004 may include domes G, which should be configured to avoid collapsing when the air bladder 2002 compresses against the skin.

External air may enter the brace laterally as shown by the air arrow R in FIG. 20. Air may flow to reach the skin 2005 via the holes D. The air may flow through the empty spaces F. The domes G of layer 2004 may keep as much as about 90% of the surface of layer 2004 out of direct contact with the skin 2005 as a result of the roof of each dome being elevated away from the skin 2005 by about 3 mm to about 5 mm.

According to this embodiment, the base of layer 2004 may be compressed against the skin 2005 with less discomfort and less compression marks. Channels or grooves E may allow the layer more flexibility as needed against the skin 2005.

The protruded membrane may be made of two layers of thermoformed EVA or similar plastic material. The upper layer may be hard enough to withstand compression from the inflated air bladder without collapsing and as such provides scaffolding functionality. The other layer 2004A may be a softer cushioning layer that may be compressed against the surface of the skin 2005.

Figure 21:
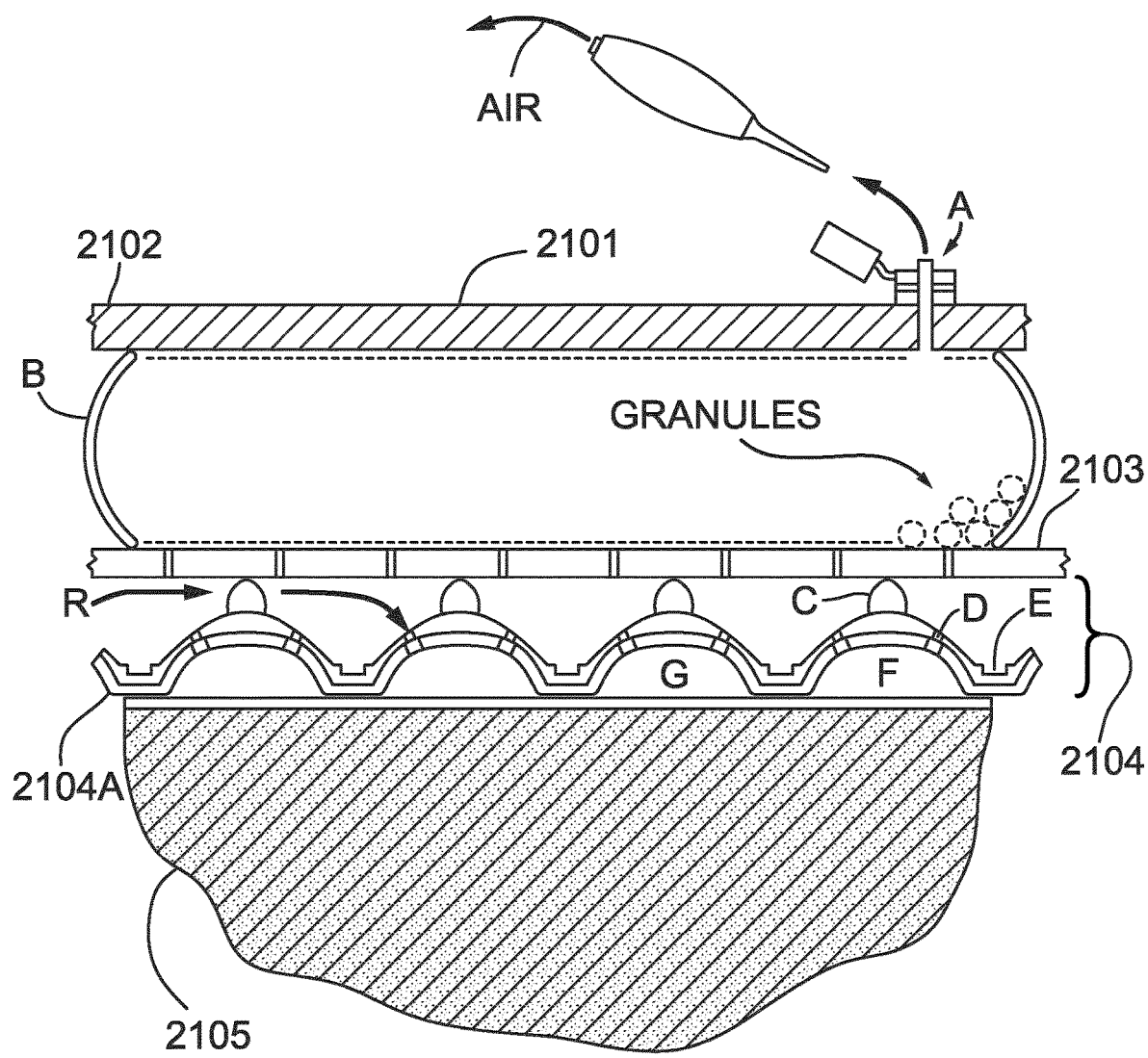
FIG. 21 is a cross-sectional view of an orthopedic support including vacuum cushion pads according to an embodiment of the invention.

FIG. 21 shows an orthopedic support including vacuum cushion pads according to an embodiment of the invention. A vacuum cushion pad, as described for example in U.S. Pat. No. 7,285,104 issued to Hassler et al on Oct. 23, 2007, may be employed which may be able to adapt to the wearer's body shape but such devices may lack features for allowing for suitable aeration. According to the embodiment shown in FIG. 21, the same features discussed herein may be applied as segments at different parts of a vacuum cushion pad 2102 having walls B and granules instead of an inflatable air bladder. Accordingly, there may be provided a Styrofoam™ scaffolding mesh or a protruded EVA layer (i.e. a layer of EVA with protrusions as described elsewhere herein) such as multi-perforated membrane 2104 of a durometer of about 30 to about 40 hardness that may have perforations D and protrusions C. The protruded EVA layer may have dual hardness with a softer layer facing the wearer's skin or sock. External air may travel from the perimeter of the walls of the support and may flow across the empty space between the protrusions C until reaching the wearer's skin 2105. Air F may flow through and accumulate inside the domes G, which may be about 4 mm to about 5 mm high. The protruded EVA layer may be bendable due to the longitudinal grooves E. A soft cushioning layer 2104A, plastic walls 2101, and mesh net layer 2103 may be included similar to as described with respect to the embodiment in FIG. 20 above.

According to a further embodiment, there may be provided an orthopedic support such as a brace which may include a vacuum cushion and the protruded EVA layer as described above and then at another location of the orthopedic support where controllable pressure is desired there may be a protruded EVA layer applied against an inflatable air bladder.

Figure 22:
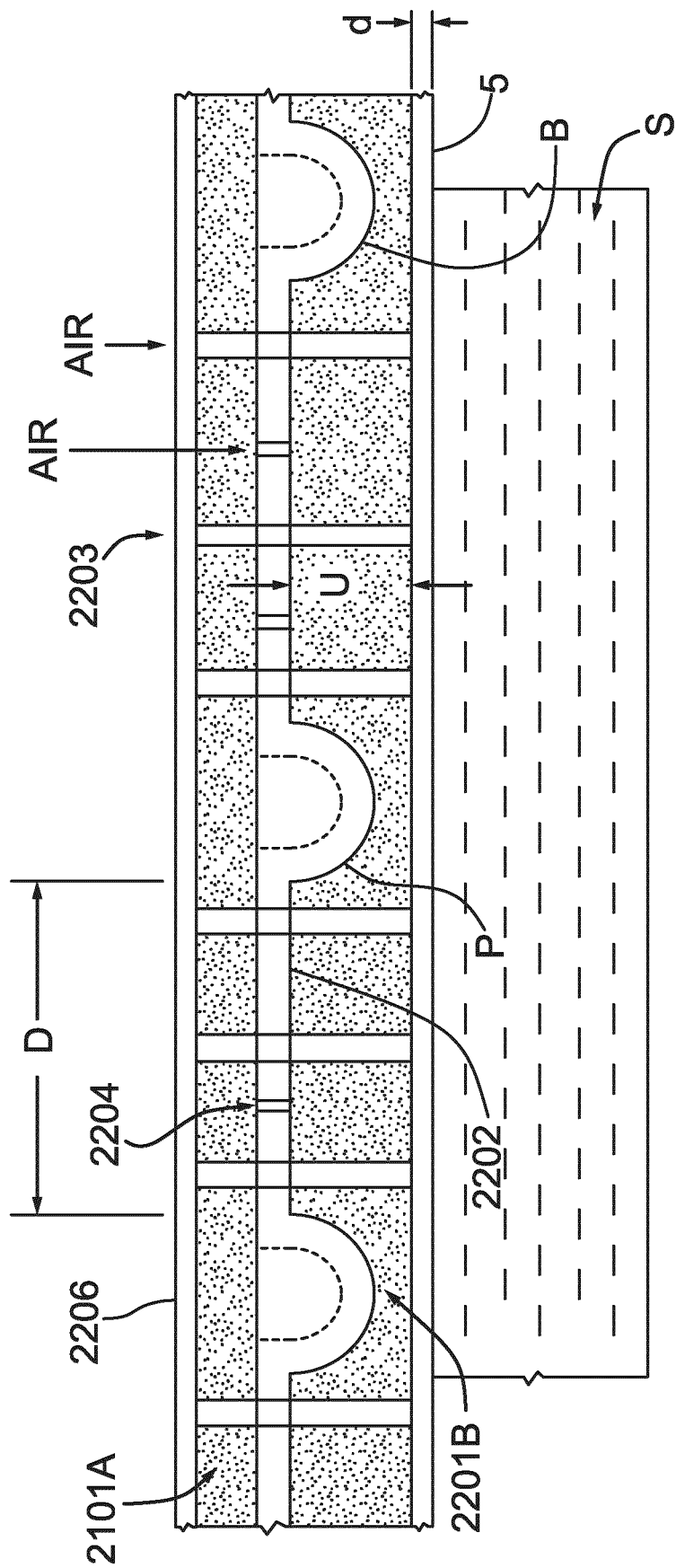
FIG. 22 is a cross-sectional view of an inner layer and an intermediate layer of an orthopedic support according to an embodiment of the invention.

FIG. 22 is a cross-sectional view of the layers of an orthopedic support according to an embodiment of the invention. Foam layers 2201A and 2201B may be laminated by a porous fabric 2206 on its outer side and may be laminated by a multi-perforated fabric 5 at its opposite or inner side. Between foam layer 2201A and foam layer 2201B there may be provided a hypoallergenic layer 2202 made of EVA, or polyurethane or Styrofoam™ or polyethylene, or any soft equivalent material. The distance D may be the distance between each protrusion P (having base B)

and may be at least three times the diameter of each protrusion P. Height U may show the uncompressed height of the foam over distance D. As the foam is compressed, the base B of each protrusion P may maintain a distance d for the wearer's skin S. The foam layers 2201A and 2201B may be equipped with internal perforations 2203 which may have diameters of about 2 mm to about 4 mm. They may be separated from each other by about 2 cm. The perforations 2203 may be through layer 2201A and layer 2201B. Layer 2202 may have a plurality of perforations 2204, which may be about 1 mm in diameter and be separated by about 3 mm from each other. Other dimensions and densities for the perforations 2203, 2204 may be used as appropriate for the particular application. As such, when the foam layers are not excessively compressed at areas a, b, c, and d, the air in these areas may flow to the wearer's skin S in part because of the presence of the protrusions P.

Figure 23:
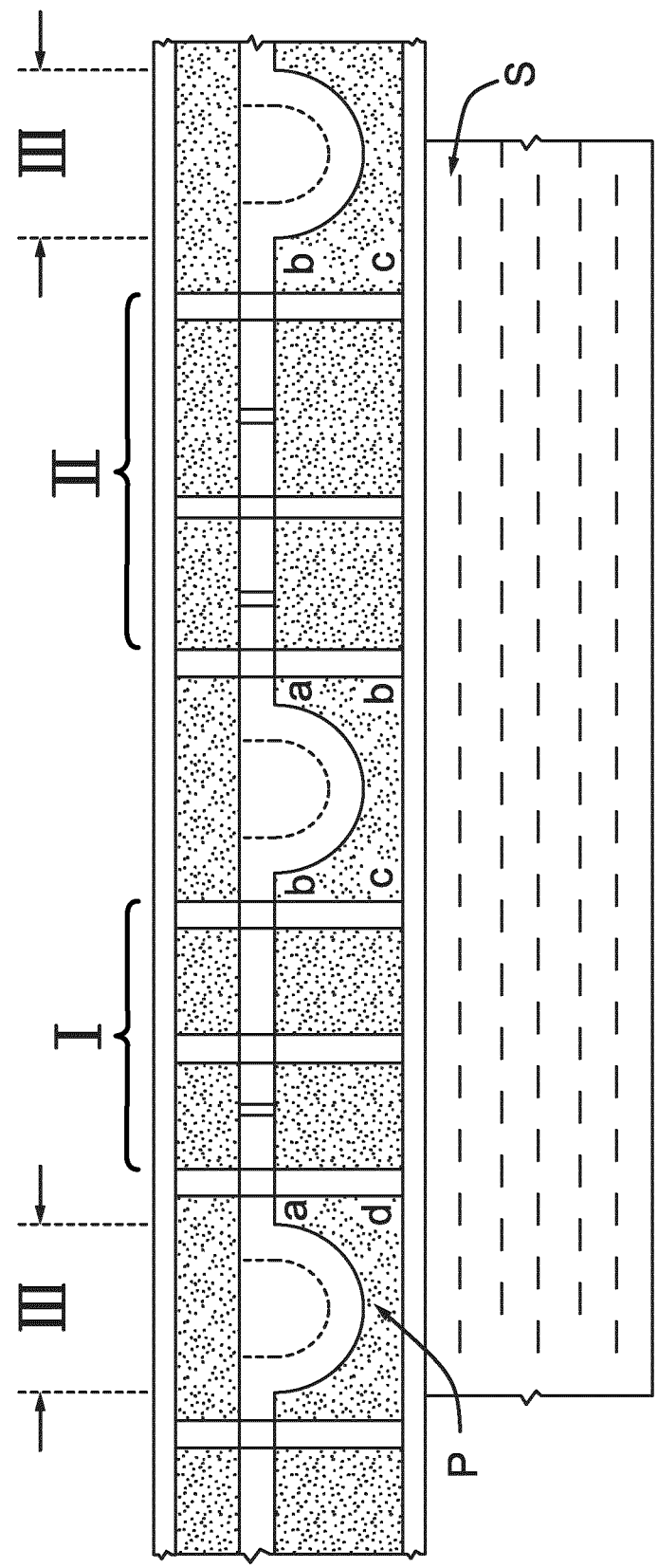
FIG. 23 is a cross-sectional view of an inner layer and an intermediate layer of an orthopedic support according to an embodiment of the invention.

FIG. 23 is a cross-sectional view of an inner layer and an intermediate layer of an orthopedic support according to an embodiment of the invention. In this figure, segment I, segment II and segment III are denoted on the left side and segment IV is denoted on the right side. Segments III and IV may have protrusions P. The support may be mounted against the skin S. Foam membranes may be compressed against the skin S and when this is done, the thickness of the padded foam may be reduced and when they are not compressed the foam membranes may then re-expand to their original thickness. The protrusions P therefore act as a scaffolding element and may help the spaces a, b, c, and d to be less compressed in segments I and II thereby ensuring external air may reach the wearer's skin.

Figure 24:
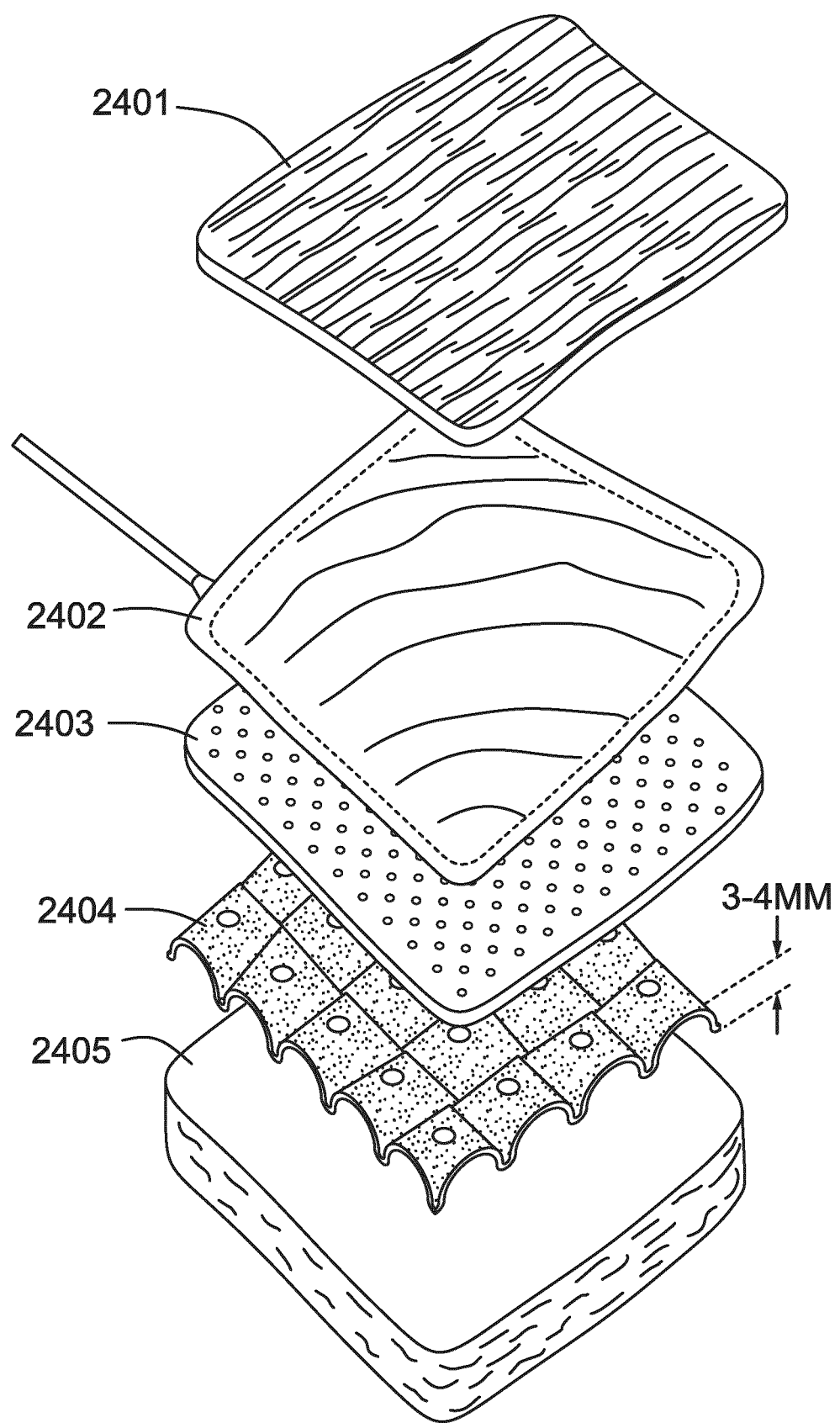
FIG. 24 is an exploded view of the layers of an orthopedic support according to an embodiment of the invention.

FIG. 24 is an exploded view of successive layers of an orthopedic support according to an embodiment of the invention. The external portion of the brace 2401 may be perforated. Air bladder 2402 may have any suitable shape for providing therapeutic compression to the wearer. For instance, it may be shaped like an "O" in which it may only have air inflated around its perimeter. It may also have divided compartments of air. A layer 2403 of mesh net or EVA is also provided which may include a plurality of holes. Layer 2403 may help the protrusions on layer 2404, which may be a dual membrane layer made of EVA as discussed above, not to deform the inflated walls of the air bladder 2402. Or, in other words, it reinforces the air bladder's walls as a scaffolding element. Layer 2404 may have holes and protrusions or domes which may have a height of about 3 mm to about 4 mm according to an embodiment. Optionally, the wearer's skin 2405 may also be covered by a wound dressing or by a stockinette or by cotton.

Figure 25D:
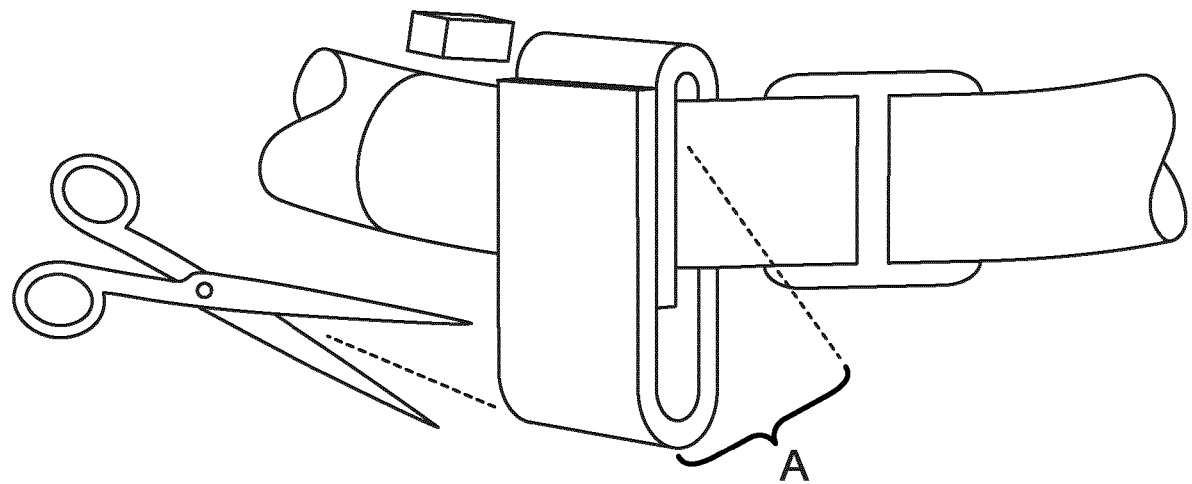

FIGS. 25(*a*)-(*c*) shows components of a securing mechanism for an orthopedic support according to an embodiment of the invention. The orthopedic supports disclosed herein may be secured to the wearer's limb by straps such as nylon straps that have hook and loop mechanisms such as Velcro™ straps. According to an embodiment, the straps may include a plurality of holes or perforations to allow external air to pass through. According to an embodiment, the orthopedic support may include a lock to help ensure that the wearer may not open the brace without permission from a caregiver. According to other embodiments, the securing mechanism may be a buckle or boot lace.

In FIG. 25(*a*), a peelable wax paper 2501 and a longitudinal tab 2502 may be provided which may be made of a semi-soft plastic material. The tab 2502 may be slid vertically downwards behind the nylon strap 2504 which may be locked by means of the buckle 2503 and Velcro™ system.

In FIG. 25(*b*), where the tab 2502 hooks the strap 2504, a peelable cover 2501 may be removed and portion 2502 of the tab may be lifted upwards towards the sticky area 2506 and this movement continues until portion A may be fully adhered to the sticky area 2506.

In FIG. 25(*c*), strap 2504 may not be opened because the underside 2505 of portion A may be fully adhered to sticky area 2506. The locking system may not be foiled by sliding it to the left side because it will be blocked from moving further by the presence of other blocking elements as shown on the left side of the lock. When the brace has to be opened, the lock may be removed by scissors.

Figure 26:
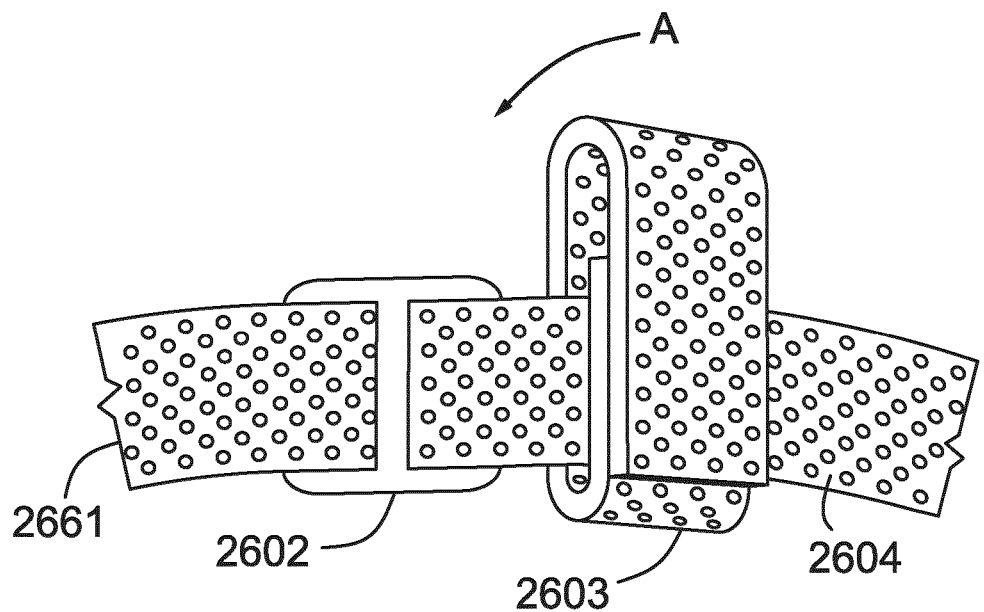
FIG. 26 is a front view of a strap and a buckle for an orthopedic support according to an embodiment of the invention.

FIG. 26 is a front view of a strap and a buckle of an orthopedic support according to an embodiment of the invention. Straps A may be made of nylon and may be secured by buckles 2602. The straps A may be positioned externally around the walls of the braces. The straps may have holes 2604 which may allow external air pass through and enter inside the brace and reach the wearer's skin. If numerous holes 2604 are added to straps A, the thickness of straps A may need to increase to compensate for the additional holes 2604 which may otherwise make straps A weaker. A buckle 2603 and a peelable cover may be included as described in FIGS. 25(*a*) and 25(*b*).

Figure 27:
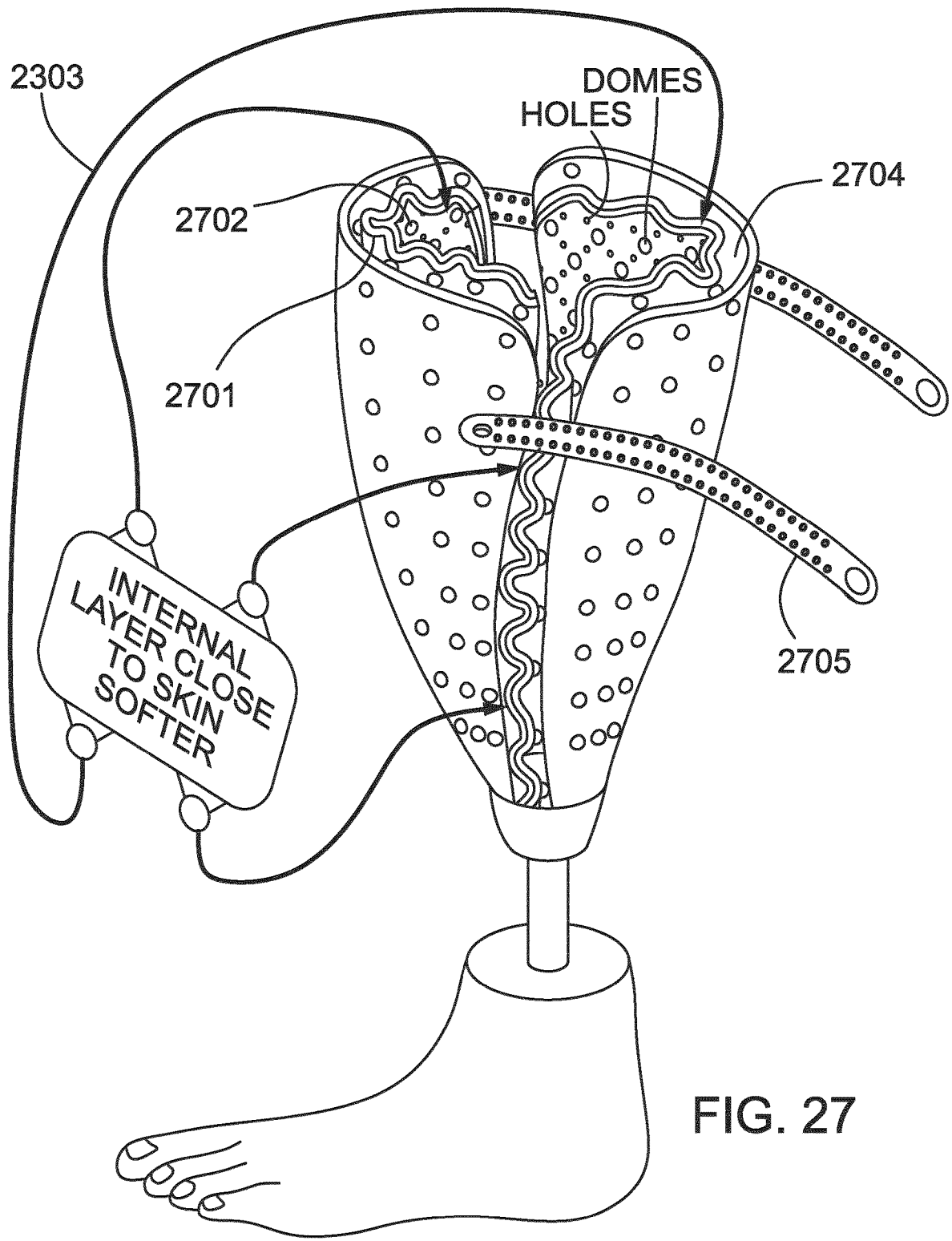
FIG. 27 is a side view of a support for use with a prosthesis according to an embodiment of the invention.

FIG. 27 is a side view of a prosthetic support for use with a prosthesis according to an embodiment. A dual hardness membrane 2701 may be included comprising an inner layer and an intermediate layer in accordance with the embodiments described for the orthopedic support above wherein the softer layer is closer to the wearer's skin and the harder side may be closer to an exterior layer such as plastic walls. The membrane 2701 may comprise hypoallergenic silicone or EVA or polyurethane material. The membrane 2701 may include holes 2702 through which air 2704 may pass through as well as domes 2703. The membrane 2701 may be enclosed by a substantially porous exterior layer which may include a securing means such as perforated belts 2705 to secure the prosthetic support over the limb of the wearer. The prosthetic support may also be secured to the prosthesis by the same or a further securing means.

Figure 28:
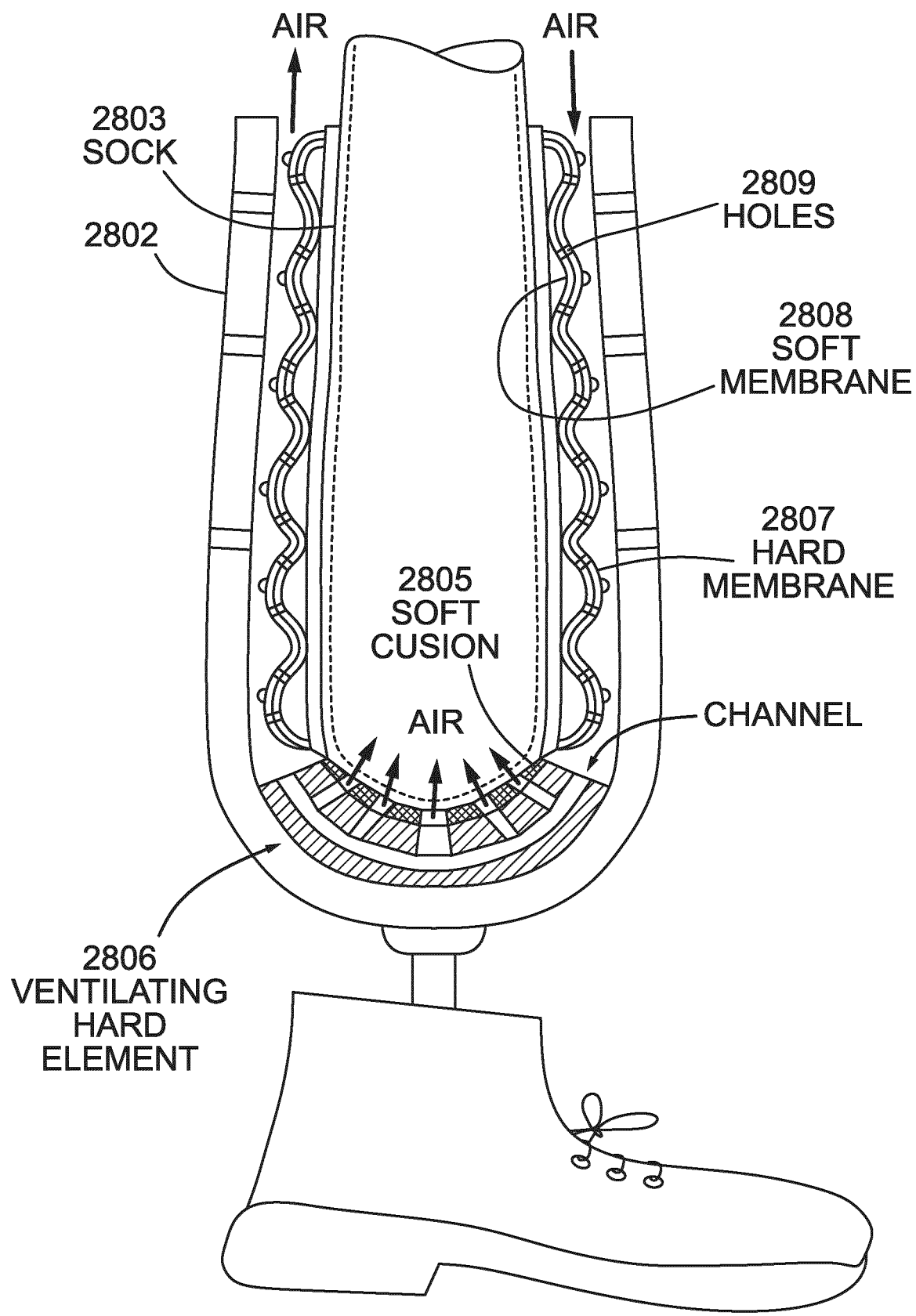
FIG. 28 is a cross-sectional view of a support for use with a prosthesis according to an embodiment of the invention.

FIG. 28 is a cross-sectional view of a prosthetic support for use with a prosthesis according to an embodiment. The prosthetic support is similar to the orthopedic supports described above, in which air may pass through the exterior layer, which may be a hard breathable surface in accordance with the embodiments described herein such as a plastic wall 2802 including a plurality of perforations or holes 2809 therein, and then pass may through perforations in an intermediate layer such as hard membrane 2807 having domes with bumps and then through perforations in a softer, cushioning inner layer such as soft membrane 2808 to the wearer's limb 2801, or optionally, first through a sock 2803 worn by the wearer. At the bottom of the limb 2801, there may be included a supportive element 2804 with transversal and radial air passageways as shown. The bottom of the limb 2801 may rest on a cushioning layer 2805 of EVA or pre-molded silicone which may have a further layer 2806 on the other side of the cushioning layer which may be a harder, scaffolding layer as shown.

It should be appreciated that although a prosthetic support for a lower leg is illustrated in FIGS. 27 and 28, it is also possible to employ a prosthetic support constructed in accordance with embodiments of the invention which may be adapted for use on a body part other than the lower leg. Further, although the illustrated prosthetic support is adapted for use on the lower leg of a human, it will be appreciated by those skilled in the art that a prosthetic support constructed in accordance with embodiments of the invention may also be used on an animal.

The present invention may be embodied in other specific forms without departing from the spirit or essential characteristics thereof. Certain adaptations and modifications of the invention will be obvious to those skilled in the art. Therefore, the presently discussed embodiments are considered to be illustrative and not restrictive, the scope of the invention being indicated by the appended claims rather than the foregoing description and all changes which come within the meaning and range of equivalency of the claims are therefore intended to be embraced therein.

What is claimed is:

1. An orthopedic or prosthetic support comprising:
   a substantially porous inner layer comprising a flexible cushioning material including a plurality of perforations extending between opposite sides of the layer;
   a substantially porous intermediate layer comprising a flexible material including a plurality of perforations extending between opposite sides of the layer and a plurality of spacer members arranged in a repeating pattern wherein the spacer members comprise domes, wherein the domes comprise bumps on top of the domes, wherein the substantially porous intermediate layer is situated substantially parallel to the substantially porous inner layer yet spaced apart by the spacer members so as to provide air passages between the intermediate layer and the inner layer and air pathways through both the plurality of perforations in the intermediate layer and the plurality of perforations in the inner layer and wherein the flexible material of the intermediate layer has greater hardness than the flexible cushioning material of the inner layer;
   a substantially porous exterior layer enclosing the intermediate layer, wherein air external to the orthopedic or prosthetic support may pass through the substantially porous exterior layer to the air pathways; and
   a securing mechanism affixed to at least the exterior layer for securing the orthopedic or prosthetic support to a living being.

2. The orthopedic or prosthetic support of claim 1, wherein the substantially porous inner layer and the substantially porous intermediate layer are enclosed by a removable envelope.

3. The orthopedic or prosthetic support of claim 2, wherein the removable envelope comprises a tubinette.

4. The orthopedic or prosthetic support of claim 1, further comprising an air bladder affixed to an inner surface of the substantially porous exterior layer.

5. The orthopedic or prosthetic support of claim 1, wherein the substantially porous exterior layer comprises a flexible breathable fabric.

6. The orthopedic or prosthetic support of claim 5, wherein the flexible breathable fabric comprises velvet.

7. The orthopedic or prosthetic support of claim 1, wherein the repeating pattern comprises a grid-like pattern.

8. The orthopedic or prosthetic support of claim 1, wherein the flexible cushioning material of the inner layer comprises ethylene-vinyl acetate (EVA).

9. The orthopedic or prosthetic support of claim 1, wherein the substantially porous exterior layer comprises thermoplastic and includes a plurality of perforations.

10. The orthopedic or prosthetic support of claim 1, wherein the securing mechanism comprises a strap.

11. The orthopedic or prosthetic support of claim 1, wherein the substantially porous intermediate layer includes a plurality of grooves in between the spacer members.

12. The orthopedic or prosthetic support of claim 1, wherein the substantially porous intermediate layer is a dual layer comprising a layer with a lower durometer adjacent to the substantially porous inner layer and a layer with a higher durometer adjacent to an inner surface of the substantially porous exterior layer.

13. The orthopedic or prosthetic support of claim 1, further comprising a substantially porous foam layer.

* * * * *